United States Patent [19]

Heym et al.

[11] Patent Number: 5,871,912
[45] Date of Patent: *Feb. 16, 1999

[54] **NUCLEIC ACID PROBES, SEQUENCES AND METHODS FOR DETECTING *MYCOBACTERIUM TUBERCULOSIS* RESISTANT TO ISONIAZID**

[75] Inventors: Beate Heym, Ville d'Avray; Stewart T. Cole, Clamart, both of France; Douglas B. Young, Middlesex, United Kingdom; Ying Zhang, Baltimore, Md.

[73] Assignee: Institut Pasteur, Paris Cedex, France

[ * ] Notice: The term of this patent shall not extend beyond the expiration date of Pat. No. 5,633,131.

[21] Appl. No.: 459,499

[22] Filed: Jun. 2, 1995

Related U.S. Application Data

[63] Continuation-in-part of Ser. No. 29,655, Mar. 11, 1993, abandoned, and Ser. No. 929,206, Aug. 14, 1992, Pat. No. 5,633,131, which is a continuation-in-part of Ser. No. 875,940, Apr. 30, 1992, abandoned, said Ser. No. 29,655, is a continuation-in-part of Ser. No. 875,940, and Ser. No. 929,206.

[51] Int. Cl.[6] .............................................. C12Q 1/68
[52] U.S. Cl. ........................... 435/6; 436/501; 536/22.1; 536/24.1; 536/24.3; 536/24.31; 536/24.32; 536/24.33; 935/77; 935/78
[58] Field of Search ....................... 435/6, 810; 436/501; 536/23.1, 24.1, 24.3–24.33; 935/77, 78

*Primary Examiner*—Ardin H. Marschel
*Attorney, Agent, or Firm*—Finnegan, Henderson, Farabow, Garrett & Dunner

[57] ABSTRACT

Multi-drug resistant strains of *Mycobacterium tuberculosis* represent a considerable threat to public health worldwide. Resistance to isoniazid (INH), a key component of anti-tuberculosis regimens, is often associated with loss of catalase activity and virulence. The katG gene, encoding HPI catalase-peroxidase, mediates INH-sensitivity and that the high level resistance encountered clinically may be due to deletions, insertions or point mutations which reduce or eliminate the expression of the catalase gene in the chromosomal region encompassing katG. INH-resistant strains of *Mycobacterium tuberculosis* are detected by nucleic acid hybridization with a unique nucleic acid sequence or by amplification techniques.

14 Claims, 20 Drawing Sheets

```
M. tuberculosis         APLNSWPDNASLDKARRLLWPSKKKYGKKLSWADLIV
E. coli                 *********V************I*Q***Q*I*****FI
B. stearothermophilus   **********N******C*GR**RNT*T*-*LGPICS
```

```
<--------------------lacZ'---------------------------->
M  T  M  I  T  P  S  L  H  A  C  R  S  T  L  E  D  P  H  P  T  L  R
ATGACCATGATTACGCCAAGCTTGCATGCCTGCAGGTCGACTCTAGAGGATCCCCATCCGACACTTCGCG
         10        20        30        40        50        60        70
katG------>
M  S  T  S  D  D  -  -  I  H  N  T  T  A  T  G  K  C  P  F  H  Q  G
*  :                       *  *  :  :  :              :
M  P  E  Q  H  P  P  I  T  E  T  T  T  G  A  A  S  N  G  C  P  V  V
GTGCCCGAGCAACACCCACCCATTACAGAAACCACCACCGGAGCCGCTAGCAACGGCTGTCCCGTCGTGG
        130       140       150       160       170       180       190

N  Q  L  R  V  D  L  L  N  Q  H  S  N  R  S  N  P  L  G  E  D  F  D
*  *  :     :  *  *        :        :  :  *  :  *        *  *
N  R  L  N  L  K  V  L  H  Q  N  P  A  V  A  D  P  M  G  A  A  F  D
AACCGGCTCAATCTGAAGGTACTGCACCAAAACCCGGCCGTCGCTGACCCGATGGGTGCGGCGTTCGACT
        250       260       270       280       290       300       310
```

FIG. 6C(2)

```
D  H  I  R  D  H  S  P  I  T  P  T  P  G  R  N  A
ATCACATCCGTGATCACAGCCCGATAACACCAACTCCTGGAAGGAATGCT
         80        90       100       110       120

G  H  D  Q  S  A  G  A  G  T  T  T  R  D  W  W  P   E.coli
*  *        :        *  :  :        *  *  *  *
G  H  M  K  Y  P  V  E  G  G  G  N  Q  D  W  W  P   M.tub
GTCATATGAAATACCCCGTCGAGGGCGGCGGAAACCAGGACTGGTGGCCC
        200       210       220       230       240

Y  R  K  E  F  S  K  L  D  Y  Y  G  L  K  K  D  L   E.coli
*        *  :  :              :  *     :  *  :
Y  A  A  E  V  A  T  S  R  L  D  A  L  T  R  D  I   M.tub
ATGCCGCGGAGGTCGCGACCAGTCGACTTGACGCCCTGACGCGGGACATC
        320       330       340       350       360
```

FIG. 10A(1)

```
GGTACCGTGAGGCGATGGGTGGCCCGGGGCCCGGCTGTCTGGTAAGCGGCCGCCCAAAACAGCTGTACTCTCGAATCCCAGTTAGTAACATGTGCTATGGAATCTCCAATGACGAGCAC
         10        20        30        40        50        60        70        80        90       100       110       120
ACTTCACCGAACCCCATTAGCCACCTCGCGGGCCTGGCGCTCGTAGTGGCCGGTGCGCTCGTAGTGGGCGGTGCGGGGCGGTGACAGTGAGAGACACCGCCATACGTGCCGAAAGCGACGACCGT
        130       140       150       160       170       180       190       200       210       220       230       240
CGACCGCAACAACGCCGGCTGGCCGGCCGAGCGCACTGCGATCGCCAGTCCCATGTTCGCCGACGGCGCCCGATCCGGTGCAATTCAGCTGCAAGGGGCCAACGTGGCCGCCACCGT
        250       260       270       280       290       300       310       320       330       340       350       360
TGACGTGGTCGTGCGCCGGCGGGCGAGCGAACTGGACTGCCACTCGCGTCGATGACGAACTCGGCACTGAACGTGCACTGGATCGTGACGGAATCGCCCCTGGCTCTGGCAGCACCGG
        370       380       390       400       410       420       430       440       450       460       470       480
CGGATGGTCAGACTCCTGCTGTGGGCACAGCGTGCCGAATTCGGTGGTCGGCAAGGATACTTCGGTCCATGCCCCGGGCACCGGACACCACTACCGGTTTACCCTCTACC
        490       500       510       520       530       540       550       560       570       580       590       600
ACCTTCCTGCCGAGGTGGTCGAAACCCTGGCTTCTCCAATTGCGCCTGGCGACAGCGGCACAGGCCCGGCTCGTCGGCCACATTCACCGGTTCGCACTGGCCATCTTGGGGCTGG
        610       620       630       640       650       660       670       680       690       700       710       720
CATCCCGCCGTGGCCTAGTTGCCTACGGTGGCAACGGTGACAGTGACAAGGCAGCAGCCTCGGTCGGAGTATGCCCGAAACGCCTACCGGCACTCGGCGGCGGATGTAC
        730       740       750       760       770       780       790       800       810       820       830       840
CGCTCCCCGTGGCTAGTTGCCTACGGTGGCAACGGTGACAGTGACAAGGCAGCAGCCTCGGTCGGAGTATGCCCGAAACGCCTACCGGCACTCGGCGGCGGATGTAC
        850       860       870       880       890       900       910       920       930       940       950       960
TGACAATCAGCAGTCCGGCATTCGCCGACGGTGCGCGATCCGCCGAACAGTACACCTGCAAAGGAGCCAATATCGCGCCCTCCGTTGACCTGGTCGGCGCCGTTTGGCGGCGACTCGTT
        970       980       990      1000      1010      1020      1030      1040      1050      1060      1070      1080
GTCGATGATCCGACCAGCCTCGCGAACCTTACGTCGTTGATCGGATCGGATGGTGAGACTCCCGGTGGCGGATCAGCCTGCCGAACTCC
       1090      1100      1110      1120      1130      1140      1150      1160      1170      1180      1190      1200
AGCGGTCAGCCGCATACACCGGCCCTGCCGCTGCCCACCTTCCGCCGTTACCCTCTACCACCTTCCGCCTGCCCTCCACTCCGCCGGACTGGCTGGGACACAA
       1210      1220      1230      1240      1250      1260      1270      1280      1290      1300      1310      1320
GCGGGCGGGGTGATCGCGGCCGCCAGCCGCCACATGCAGGCCCGGCTCATCGGAACATACGAAAGGCTGATCGATCCACCCGATCCGGTCCTAGCAGACG
       1330      1340      1350      1360      1370      1380      1390      1400      1410      1420      1430      1440
CCTGTCACGCTAGCCAAAGTCTTGACTGATTCCAGAAAAGGGAGTCATATTGTCTAGTGTGTCCTCTATACCGGACTACGCCGAACAGCTCCGGACTCGGCGGTGACCCGACC
       1450      1460      1470      1480      1490      1500      1510      1520      1530      1540      1550      1560
```

FIG. 10A(2)

```
GCGGTCGCCGTCCTCGGAAGCAGTGAATGCATCCACACGCCGACACGGAAACGATTTTCGGTGCCGTGCGTTTGCCTGCTGCGGCCTGCGCGACGATATCCGGCAAGCCGTGTACGACGTGCTGCAT
     1570      1580      1590      1600      1610      1620      1630      1640      1650      1660      1670      1680
GCCCTGACGCGCCGGGCTTGGTGCCGAAAGATCCAACCCTCGGCTCCGTCCGGCGCCTCCGAGTCCAGGGTCGGCGACCATCACATGCTCTGCCGGTCTTGCCGGTTATGCC
     1690      1700      1710      1720      1730      1740      1750      1760      1770      1780      1790      1800
GATGTCGACTGTGCTGTTGGCGAGGCACCCTGTCTGACGGCCTTCGGACCATAACGGCTTCCTGTTGACGAGGCGGAGTCATCTACTGGGGTCATCTACTCCTGATTGTTCGATATCCGAC
     1810      1820      1830      1840      1850      1860      1870      1880      1890      1900      1910      1920
                                        M   P   E   Q   H   P   P   I   T   E   T   T   T   G   A   A   S   N   G   C   P
ACTTCGGATCACATCCGTGATCACAGCCCGATAACACCAACTCCTGAAGGAATGCTGTGCCCGAGCAACACCACCATTACAGAAACCACCGGAGCCGTAGCAACGGCTGTCC
     1930      1940      1950      1960      1970      1980      1990      2000      2010      2020      2030      2040
 V   V   G   H   M   K   Y   P   V   E   G   G   G   N   Q   D   W   P   N   R   L   N   L   K   V   L   H   Q   N   P   A   V   A   D   P   M   G   A   A
CGTCGTCGGCCATATGAAATATCCCGTCGAGGGTGGCGGGAACCAGGACTGGCCCAACCGGCTCAATCTGAAAGTACTGCACCAAAACCCGGCCGTCGCTGACCCGATGGGTGCCGGC
     2050      2060      2070      2080      2090      2100      2110      2120      2130      2140      2150      2160
 F   D   Y   A   A   E   V   A   T   S   R   L   D   A   L   T   R   D   I   E   E   V   M   T   T   S   Q   P   W   P   A   D   Y   G   H   Y   G   P   L
GTTCGACTATGCCGCGGAGGTCGCGCCAGTCGCGCCTGGACGTCGACTTGACGCGTCGAGGAAGTGATGACAATCGAGGAAGTGATGACCACCTCGGCAGCCTGGTGGCCCCGGACTACGGCCACTACGGCCCGCT
     2170      2180      2190      2200      2210      2220      2230      2240      2250      2260      2270      2280
 F   I   R   M   A   W   H   A   A   G   T   Y   R   I   H   D   G   R   G   G   A   G   G   G   M   Q   R   F   A   P   L   N   S   W   P   D   N   A   S   L
GTTTATCCGAATGGCCACGCTGCGGGCACGCTGCCGCTGCACTTCGCCATCGACGACGGCCGCGGCGGCGCCGGCGGCGGGATGCAGCGGTTCGCGCCCCGCTTAACAGCTGCCCGACAACGCCAGCTT
     2290      2300      2310      2320      2330      2340      2350      2360      2370      2380      2390      2400
 D   K   A   R   R   L   L   W   P   V   K   K   K   Y   G   K   K   L   S   W   A   D   L   I   V   F   A   G   N   R   C   A   R   N   R   W   A   S   R   R
GGACAAGGCGCGCCGGCTGCTGTGGCCGGTCAAGAAGAAGTACGGCAAGAAGCTCTCATGGGCCGACCTGATTGTTTTCGCCGGCAATCGATGGCTTCAAGACG
     2410      2420      2430      2440      2450      2460      2470      2480      2490      2500      2510      2520
```

FIG. 10A(3)

```
  S  G  S  A  S  G  V  D  Q  W  E  T  D  E  V  Y  W  G  K  E  A  T  W  L  G  D  D  G  Y  S  V  S  D  L  E  N  P  L  A  A
TTCGGGTTCGGCTGCAGTGGACCAGTGGGAGACCGATGAGTCTATTGGGCAAGGAAGCCACCTGGCTCGGCGATGACGGTTACAGCTGAGACGGATCTGAGAACCCGCTGGCCGC
         2540       2550       2560       2570       2580       2590       2600       2610       2620       2630       2640

V  Q  M  G  L  I  Y  V  N  P  E  A  P  N  G  N  P  D  D  P  M  A  A  A  V  D  I  R  E  T  F  R  R  M  A  M  N  D  V  E  T
GGTGCAGATGGGGCTGATCTACGTGAACCCGGAGGCGCCAACGGCAACCCGGACGACCCGATGGCCGCCGCGGTCGACATTCGCGAGACGTTTCGGCGCATGGCCATGAACGACGTCGAAAC
         2650       2660       2670       2680       2690       2700       2710       2720       2730       2740       2750       2760

A  A  L  I  V  G  G  H  T  F  G  K  T  H  G  A  G  P  A  D  L  V  G  P  E  P  E  A  A  P  L  E  Q  M  G  L  G  W  K  S
AGCGGCGCTGATCGTCGGCGGTCACACTTTCGGTAAGACCCATGGCGCCGGCCCGGCCGATCTGGTCGGCCCGGAACCCGAAGGCTGCTCCCGAGGCTGGGCTGGGCTGGAAGAG
         2770       2780       2790       2800       2810       2820       2830       2840       2850       2860       2870       2880

S  Y  G  T  G  T  G  K  D  A  I  T  S  G  I  E  V  V  W  T  N  T  P  T  K  W  D  N  S  F  L  E  I  L  Y  G  Y  E  W  E
CTCGTATGGCACCGGCACCGGTAAGACCGGATCGAGGTCGTATGGACGAATGGACAACACCCCGACGAAATGGACAACAGTTCCTCGAGATCCTGTACGGCTACGAGTGGGA
         2890       2900       2910       2920       2930       2940       2950       2960       2970       2980       2990       3000

L  T  K  S  P  A  G  A  W  Q  Y  T  A  K  D  G  A  G  T  I  P  D  D  P  F  G  G  P  G  R  S  P  T  M  L  A  T  D  L
GCTGACGAAGAGCCCTGCTGGCGCTTGGCAGTACACCGCCAAGGACGGCGCCGGTGCCAGGGCGCTCCCGGATCCCCGACGATGCTGGCCACTGACCT
         3010       3020       3030       3040       3050       3060       3070       3080       3090       3100       3110       3120

S  L  R  V  D  P  I  Y  E  R  I  T  R  R  W  L  E  H  P  E  E  L  A  D  E  F  R  K  A  W  Y  K  L  I  H  R  D  M  G  P
CTCGCTGCGGGTGGATCCGATCTATGAGCGGATCACGCGGCGTCGCTGGCTGGAACACCCGGAGGAATTGGCCGACGAGTTCCGCAAGGCCTGGTACAAGCTGATCCACCGAGACATGGGTCC
         3130       3140       3150       3160       3170       3180       3190       3200       3210       3220       3230       3240

V  A  R  Y  L  G  P  L  W  P  K  Q  T  L  L  W  Q  D  P  V  P  A  V  S  T  T  S  S  A  K  Q  I  A  S  L  K  S  Q  I  R
CGTTGCAGATACCTTGGGCCGCTGGTCCCCAAGCAGACCCTGCTGTGGCAGGATCCGGTCCCGGCAGTCAGCACGACGTCGTCGGCGAAGCAGATTGCCAGCCTTAAGAGCCAGATCCG
         3250       3260       3270       3280       3290       3300       3310       3320       3330       3340       3350       3360
```

FIG. 10A(4)

```
A  S  G  L  T  V  S  Q  L  V  S  T  A  W  A  A  A  S  S  F  R  G  S  D  K  R  G  G  A  N  G  G  R  I  R  L  Q  P  Q  V
GGCATCGGGATTGACTGTGTCTCACAGCTAGTTTCGACGTTGTCGTCGCTGTAGGAGCGGGGGCATGGGCGCCGGGGCGGCGCCAAGCGTGGTGTCGCATCCGCCTGCAGCCACAAGT
      3380        3390        3400        3410        3420        3430        3440        3450        3460        3470        3480

G  W  E  V  N  D  P  D  G  S  A  Q  G  H  S  H  P  E  E  I  Q  E  S  F  T  R  R  G  N  I  K  V  S  F  A  D  L  V  V  L
CGGGTGGGAGTCAACGACCCCGACGGATCTGCGCAAGGTCATTCGCACCCTGAAGAGATCCAGGAGTCATTCACTCGGCGCGGGGAACATCAAAGTGTCCTTCGCCGACCTCGTCGTGCT
      3490        3500        3510        3520        3530        3540        3550        3560        3570        3580        3590        3600

G  G  C  A  P  L  E  K  A  A  K  A  A  G  H  N  I  T  V  P  F  T  P  G  P  H  D  A  S  Q  E  Q  T  D  V  E  S  F  A  V
CGGTGGCTGTGCGCCACTAGAGAAAGCAGCAAAGGCGGCCGGGCACAACATCACGGTGCCCTTCACCCCGGGCCCGCACGATGCTCGCAGGAACAAACGACGTGGAATCCTTTGCCGT
      3610        3620        3630        3640        3650        3660        3670        3680        3690        3700        3710        3720

L  E  P  K  A  D  G  F  R  N  Y  L  G  K  G  N  R  C  R  P  S  T  S  L  L  D  K  A  N  L  L  T  L  S  A  P  E  M  T  V
GCTGGAGCCCAAGGCAGATGGCTTCCGAAACTACCTCGGAAAAGGGCAACCGTTGCCGGCCGAGTACATCGCTCCTGCTACGCTCAGTGCCCTGAGATGACGGT
      3730        3740        3750        3760        3770        3780        3790        3800        3810        3820        3830        3840

L  V  G  G  L  R  V  L  G  A  N  Y  K  R  L  P  L  G  V  F  T  E  A  S  E  S  L  T  N  D  F  F  V  N  L  L  D  M  G  I
GCTGGTAGGCGGCCTGCGCGTCCTCGGCGCCAACTACAAGCGGCTTCCGCTTGGGCGTGTTCACCGAGGCCTCCGAGTCACTGACTAACGACTTCTTCGTGAACCTGCTCGACATGGGTAT
      3850        3860        3870        3880        3890        3900        3910        3920        3930        3940        3950        3960

T  W  E  P  S  P  A  D  D  G  T  Y  Q  G  K  D  G  S  G  K  V  K  W  T  G  S  R  V  D  L  V  F  G  S  N  S  E  L  R  A
CACCTGGGAGCCCTTCGCCAGACGCAGATGACGGGCACCTACCAGGGCAAGGATGGCAGTGGCAAGGTGAAGTGGACCGGCAGCCGGGTCGACCTGGTCTTCGGGTCCAACTCGGAGTTGCGGGC
      3970        3980        3990        4000        4010        4020        4030        4040        4050        4060        4070        4080

L  V  E  V  Y  A  P  M  T  R  Q  A  K  F  V  T  G  F  V  A  A  W  D  K  V  M  N  L  D  R  F  D  V  R  *
GCTTGTCGAGGTCTATGCCCCGATGACGCGGCAGGCGAAGTTCGTGACAGGATTCGTGGCTGCTTGGGACAAGGTGATGAACCTCGACAGGTTCGATGTCGGTTGATCGG
      4090        4100        4110        4120        4130        4140        4150        4160        4170        4180        4190        4200
```

FIG. 10A(5)

```
CCCTGCCCGCGATCAACCACCGCCGAACCCCGCAGCACCCCGCGAGCTGACCGGCTCGCCGGGGTGCTGCTGTTTGCCCGGCGGATTGTCAGACCCCGCGTGTCGTCGCACGGACG
    4210      4220      4230      4240      4250      4260      4270      4280      4290      4300      4310      4320
CACGAGACGGGGATGACGAGACCGGATGAGGAGAAAGGGCGCCGAAATGTGCTGGATGTGCGATCACCCGGAAGCCACCCGCGAGGAGTACCTCGACGAGGTGTACGGGATAATGCTCA
    4330      4340      4350      4360      4370      4380      4390      4400      4410      4420      4430      4440
TGCATGGCTGGGCGGTACAGCACGTGGAGTGCGACGGCCATTTGCCTACACGGTTGGTCTAACCCGGCGTTGCCGAACTGGTGGTGCCGAACCCTCTCGCCCACGACGTGGGC
    4450      4460      4470      4480      4490      4500      4510      4520      4530      4540      4550      4560
AGCGGTTGTTGAACATGCCGTCGAGGGCTCTGTCGGTGACTTGCTGACTCCCGGTATGTAGACCACCTCAAAGCCGGCCCTCTTGTCGAAACGGTCCAGGTACACATCCGACGCGC
    4570      4580      4590      4600      4610      4620      4630      4640      4650      4660      4670      4680
ATTTGTATTGTGCGATCGCCCATCTTTGCGCACAAGGTGACGGCCTTGCAGTTGGTGTGGGCCGACCGGTCGCTGGCGTGGGCGGACTTCGACGAAGGTCGCGGTACC
    4690      4700      4710      4720      4730      4740      4750      4760      4770      4780      4790
```

FIG. 10B(1)

```
     701         711         721         731         741         751
    --T----    --T--     --CGAAGGCT  GACGCCG---   --CGGCATCC  CTGGCGAG-G  TGGTCG-AAA
     *          *          *** **  *  *  ***          **** *      **** **  *  ** ** ***
    GGTACCGTGA  GGCGATGGGT  GGC-CCGGGG  CCCGGC-TGT  CTGGTAAGCG  CGGCCGCAAA
     1           11          21          31          41          51
     761         771         781         791         801         811
    CC--CTGG-C  TTCTCCAATT  GCGCCTG---  GCGACAATGA  T-CAATATGG  AATCGACAGT
     *   ***    *  * ***  ***     *  ** *       *  ******   *  *  ****  ****    ** *
    ACAGCTGTAC  T-CTCGAAT-  -C-CCAGTTA  GTAACAATG-  TGC--TATGG  AATCTCCAAT
     61          71          81          91          101         111
     821         831         841         851         861         871
    GGCG--CACG  CATTTCACCG  GTTCGCACTG  GCCATCTTGG  GGCTGGCGCT  CCCCGTGGCG
     * **  ***   * *******    * **  *   **** *   **  **********   *   ******
    GACGAGCAC-  -ACTTCACCG  AACCCCATTA  GCCACCGCGG  GGCTGGCGCT  CGTAGTGGCG
     121         131         141         151         161         171
     881         891         901         911         921         931
    CTAGTTGCCT  ACGGTGGCAA  ---CGGTGAC  AGTCGAAAGG  CGGCGGC---  CGTGGCGCCG
     ** * ** **  *** ***      ******  ****** **   *  ** *     ***     ****
    CTGGGTGGCT  GCGGGGGCGG  GGGCGGTGAC  AGTCGAGAGA  CACCGCCATA  CGT---GCCG
     181         191         201         211         221         231
     941         951         961         971         981         991
    AAAGCAGCAG  CG-CTCGGTC  G--G--AGTA  TGCCCGAAAC  GCCTACCGGC  GATGT-ACTG
     ***** * *   ** ** ** *  *  *         *** *    * ***  *** ***  * *    ****
    AAAGC-G-A-  CGAC-CG-TC  GACGCAACAA  CGCCGG---C  GCCGGCCGCC  GA-GCCACTG
     241         251         261         271         281         291
     1001        1011        1021        1031        1041        1051
    ACAATCAGC-  AGTCCGGCAT  --TCGCCGAC  GGTGCGCCGA  TCCCGGAACA  GTACACCTGC
     ** *** **   *****  ***     *******  ** **  ****  ******    **  * **  ****
    ACGATC-GCC  AGTCC--CAT  GTTCGCCGAC  GGCGCCCCGA  TCCCGGTGCA  ATTCAGCTGC
     301         311         321         331         341         351
     1061        1071        1081        1091        1101        1111
    AAAGGAGCCA  ATATCGCGGC  CTCCGTTGAC  CTGGTCGGCG  CC-GTTTGGC  G-GCG-----
     ** ** ****  *   *  ** **  * *******   ****** **  ** *    *** * ***
    AAGGGGGCCA  ACGTGGCCGC  CACCGTTGAC  GTGGTCGTCG  CCCGC--GGC  GAGCGAACTG
     361         371         381         391         401         411
     1121        1131        1141        1151        1161        1171
    -CACTCGTTG  TCGATGATCC  GGAC-CACCT  CG-CGAACCT  -TACGTCCAT  TGGATCGTGA
     *******  *  * *******  **  *** *  *  * ** ** **  * ***** **  **********
    GCACTCGTCG  TCGATGACCC  CGACGCGG-T  CGGCGGAC-T  GTACGTGCAC  TGGATCGTGA
     421         431         441         451         461         471
```

FIG. 10B(2)

```
     1181       1191       1201       1211       1221       1231
   TCGGGATCGC CCCTGG-TGC TGGCAGCA-- GCCGATGGTG AGACTCCCGG TGGCGGA-AT
   *** ***** ****** * * ********   ** ****** ******* *  *** **  *
   CCGGAATCGC CCCTGGCT-C TGGCAGCACG GCGGATGGTC AGACTCCTGC TGGTGGGCA-
    481        491        501        511        521        531
     1241       1251       1261       1271       1281       1291
   CAGCCTGCCG AACTCCAGCG GTCAGCCCGC ATACACCGGC CCTGCCCGC CGGCGGGCAC
   **** ***** ** **  * * *** **   * ****  ***  ** ****** **********
   CAGCGTGCCG AATTCTGGTG GTCGGCAAGG ATACTTCGGT CCATGCCCGC CGGCGGGCAC
    541        551        561        571        581        591
     1301       1311       1321       1331       1341       1351
   CGGGACACAC CACTACCGGT TTACCCTCTA CCACCTTCCT GCCGTGCCTC CA-CTCGC--
   ********** ********** ********** ********** * ** ** ** ** ** **
   CGGGACACAC CACTACCGGT TTACCCTCTA CCACCTTCCT GTCGCGC-TC CAGCT-GCCA
    601        611        621        631        641        651
     1361       1371       1381       1391       1401       1411
   --GGACTGG CT--GGGA-- CACAAGCGGC GCGGGTGATC GCGCAGGCCG CCACCATG-C
     ****   * *  ****   * ******** * ** ***  ** ****** *** *   * *
   CCGGGA---G CCACGGGAGT C-CAAGCGGC ACAGGCGATA GCACAGGCCG CCAGC--GAC
    661        671        681        691        701        711
     1421       1431       1441       1451       1461
   AGGCCCGGCT CATCGGAACA TACGAAGGCT GATCCACCCG CCATCC
   ********** * **** ***
   AGGCCCGGCT CGTCGGCACA ---------- ---------- ------
    721        731        741        751        761
```

FIG. 12(1)

```
                                                                                                                              100
{mtkatg} MPEQHPPITE TTTGAASNGC PVVGHMKYPV EGGGNQDWMP NRLNLKVLHQ NPAVADPMGA AFDYAAEVAT SRLD...ALT RDIEEVMTTS QPWWPADYGH
{eckatg} ..MSTSDDIH NTTATGKCPF HQGGHDQSAG AGTTRDWMP  NQLRVDLLNQ HSNRSNPLGE DFDYRKEF..  SKLDYY.GLK KDLKALLTES QPWWPADWGS
{stkatg} ..MSTSDDIH NTLSTGKCPF HQGGHDRSAG AGTASRDWMP NQLRVDLLNQ HSNRSNPLGE DFDYRKEF..  SKLDYYSALK GDLKALLTDS QPWWPADWGS
{bspera} ......MENQ NRQNAAQCPF HESVTNQSS. NRTTNKDWMP NQLNLSILHQ HDRKTNPHDE EFNYAEEFQ.  .KLDYQ.ALK EDLRKLMTES QDWWPADYGH
{ccp}    .......... .......... .......... .......... ...TTPLVHV ASVEKGRSYE DFQ......  .KVYNAIALK .....LRED  DEY..DNYIG
Consensus --MST-DDTH NTT---KCPF HQGGHDQSAG AGTTNRDWMP NQL--DLLHQ HSNRSNPLGE DFDY-KEF--  SKLDYY-ALK -DLKALLTES QPWWPADYG-
        101                                                                                                             200
{mtkatg} YGPLFIRMAW HAAGTYRIHD GRGGAGGGMQ RFAPLNSWPD NASLDKARRL LWPVKKKYGK KLSWADLIVF AGNRCARNRW ASRRSGSASG ...VDQWETD
{eckatg} YAGLFIRMAW HGAGTYRSID GRGGAGRGQQ RFAPLNSWPD NVSLDKARRL LWPIKQKYGQ KISWASLFIL AGNVALENSG FRTFGFGAGR ....EDWEPD
{stkatg} YVGLFIRMAW HGAGTYRSID GRGGAGRGQQ RFAPLNSWPD TVSLDKARRL LWPIKQKYGQ KISWADLFIL AGNVALENSG FRTFGFGAGR ...EDWEPD
{bspera} YGPLFIRMAW HSAGTYRIGD GRGGASTGTQ RFAPLNSWPD NANLDKARRC YGRSKRNTGT K.SLGPICSF WRAMSLLNRW VEKRLDSAAG PLTSGIRKKT
{ccp}    YGPLVLRLAW HISGTWDKHD NTGGSYGGTY RFKKEFNDPS NAGLQNGFKF LEPIHKEFP. WISSGDLFSL GGVTAVQEMQ GPKIPWRCGR VDTPEDTTPD
Consensus YGPLFIRMAW HGAGTYR--D GRGGAG-G-Q RFAPLNSWPD NASLDKARRL LWPIK-KYGQ KISWADLFIL AGNVALEN--  FR--GF-AGR --TEDWEPD
                                      N138
                R W H108
        201                                                                                                             300
{mtkatg} .EVYWGKEAT WLGDDGYSVS DLENPLAAVQ MGLIYVNPEA PNGNPDPMAA AVDIRETFRR MAMNDVETAA LIVGGHTFGK THGAGPADLV GPEPEAAPLE
{eckatg} LDVNWGDEKA WLTHR.HPEA LAKAPLGATE MGLIYVNPEG PDHSGEPLSA AAAIRATFGN MGMNDEETVA LIAGGHTLGK THGAGPTSNV GPDPEAAPIE
{stkatg} LDVNWGDEKA WLTHR.HPEA LAKAPLGATE MGLIYVNPEG PNHSGEPLSA AAAIRATFGN MGMNDEETVA LIAGGHTLGK THGPAAASHV GADPEAAPIE
{bspera} FIGDRKKSGS PLNAIPVIAS SKTRSPRANG VNLRQPRRAG RQAGSKSRGI SA...ETFRR MGMNDEETVA LIAGGHTFGK AHRGGPATHV GPEPEAAPIE
{ccp}    .........NG RL....... .......... .......... ....PDADKD AGYVRTFFQR LNMNDREVVA LM.GAHALGK TH........ ..........
Consensus LDVNWG-EKA WLTHR-HPE- LAKAPLGATE MGLIYVNPEG PNHS--PLSA AAAIR-TF-R MGMNDEETVA LIAGGHTLGK THGAGPASHV GP-PEAAPIE
                                                                                          H269  TH275
        301                                                                                                             400
{mtkatg} QMGLGWKSSY GTCTGKDAIT SGIEVVWTNT PTKWDNSFLE ILYGYEWELT KSPAGAWQYT AKDGAGAGTI PDPFGGPGR. ..SPTMLATD LSLRVDPIYE
{eckatg} EQGLGWASTY GSGVGADAIT SGLEVVWTQT PTQWSNYFFE NLFKYEWVQT RSPAGAIQFE AVD..APEII PDPFDPSKKR ..KPTMLVTD LTLRFDPEFE
```

FIG. 12(2)

```
                                                                                                                    D380
{stkatg}    AQGLGWASSY GSGVGADAIT SGLEVVWTQT PTQWSNYFFE NLFKYEWVQT RSPAGAIQFE AVD..APDII PDPFDPSKKR XXKPTMLVTD LTLRFDPEFE
{bspera}    AQGLGWISSY GKGKGSDTIT SGIEGAWTPT PTQWDTSYFD MLFGYDWWLT KSPAGAWQWM AVDPDEKDLA PDAEDPSKK.  ..........  .VPTMMTTD LALRFDPEYE
{ccp}       .......... ......LKN  SGYEGPWGAA NNVFTNEFYL NLLNEDWKLE KNDANNEQWD SKSGY.....  ..........  ..........  ...MMLPTD YSLIQDPKYL
Consensus   AQGLGWASSY GSGVGADAIT SG-EVVWTQT PTQW-N-FFE NLF-YEWVLT KSPAGA-Q-E AVDG-APDII PDPFDPSKKR --KPTMLVTD L-LRFDPEYE
                                W320                                                                D380         500

{mtkatg}    RITRRWLEHP EELADEFRKA WYKLIHRDM. .......... ...GPVARYL GPLVPKQTLL WQDPVPAVST TSSAKQIASL KSQIRASGLT VSQLVSTAWA AASSFRGSDK
{eckatg}    KISRRFLNDP QAFNEAFARA WFKLTHRDM. .......... ...GPKSRYI GPEVPKEDLI WQDPLPQPIY NPTEWDIDL  KFAIADSGLS VSELVSVAWA SASTFRGGDK
{stkatg}    KISRRFLNDP QAFNEAFARA WFKLTHRDM. .......... ...GPKARYI GPEVPKEDFI WQDPIPEVDY ELTEAEIEEI KAKILNSGLT VSELVKTAWA SAA..RSATR
{bspera}    KIARRFHQNP EEFAEAFARA WFKLTHRDM. .......... ...GPKTRYL GPEVPKEDFI WQDPIPEVDY ELTEAEIEEI KAKILNSGLT VSELVKTAWA SAA..RSATR
{ccp}       SIVKEYANDQ DKFFKDFSKA FEKLLENGIT FPKDAPSPFI FKTLEEQGL. .......... .......... .......... .......... .......... ..........
Consensus   KISRRFLNDP E-F-EAFARA WFKLTHRDM- ---GPK-RYI GPEVPKEDLI WQDP-PQ--Y -PTE-DII-L KAAIAASGL- VSELVS-AWA SASTFRGGDK
                     401                                                                                         500

{mtkatg}    RGGA.NGGRI RLQPQVGWEV NDPDGSAQGH SHPEEIQESF TRRGNIKVSF ADIVLGGCA  PLEKAAKAAG HNITVPF.... TPGPHDASQE QTDVESFAVL
{eckatg}    RGGA.NGARL ALMPQRDWDV N..AAAVRAL PVLEKIQ... .......... .KESGKASL  ADIIVLAGVV GVEKAASAAG LSIHVPF...  APGRVDARQD QTDIEMFELL
{stkatg}    RGGA.NGARL ALAPQRDWDV N..AVAARVL PVLEEIQ... .......... ..KTTNKASL ADIIVLAGVV GIEQAAAAAR VSIHVPF... PPGRVDARHD QTDIEMFSLL
{bspera}    ISAATNGRRI RLAPQKDWEV NEPERLAKVL SVLRGHPA.. .......... ..RTAEKSKH RRLDRLGGTL TWKTQPATPA LMSKCHFSLA AAMRHKSKPM SKALPCWNRS
{ccp}       .......... .......... .......... .......... .......... .......... .......... .......... .......... ..........
Consensus   RGGA-NGAR- -LAPQRDW-V N-P--AARVL -VLEEIQ--- ---T--KASL AD-IVL-GVV G-EKAAAAAG LSIHVPF--- APGR-DARQD QTDIEMF-LL
                     501                                                                                         601

{mtkatg}    EPKADGFRN. ...YLGKGNR CRPSTSLLDK ANLLTLSAPE MTVLVGGLRV LGANYKRLPL GVFTEASESL TNDFFVNLLD MGITWEPSPA DDGTYQGKD.
{eckatg}    EPIADGFRN. ...TRARLDV STTESLLIDK AQQLTLTAPE MTALVGGMRV LGGNFDGSKN GVFTDRVGVL SNDFFVNLLD MRYEWKATDE SKELFEGRDR
{stkatg}    EPIADGFRN. ...YRARLDV STTESLLIDK AQQLTLTAPE MTVLVGGMRV LGTNFDGSQN GVFTDKPGVL STDFFANLLD MRYEWKPTDD ANELFEGRDR
{bspera}    QMASATIKSK STRFRRKSCS STKPSSSADR PRNDGLSWR. .........FAR VGPNYRHLPH GVFTDRIGVL TNDFFVNLLD MNYEWVPTDS ..GIYEIRDR
{ccp}       .......... .......... .......... .......... .......... .......... .......... .......... .......... ..........
Consensus   EPIADGFRN- ---YRA-LDV STTES-LIDK AQQLTL-APE MTVLVGGMRV LG-N-DG-PN GVFTDR-GVL -NDFFVNLLD MRYEWKPTD- ---L-EGRDR
                     601                                                                                         700
```

FIG. 12(3)

```
          701                                                                           767
{mtkatg}  GSGKVKWTGS RVDLVRGSNS ELRALVEVYA PMTRQAKFVT GFVAAWDKVM NLDRFDVR.. ........
{eckatg}  ETGEVKFTAS RADLVFGSNS VLRAVAEVYA SSDAHEKFVK DFVAAWVKVM NLDRFDLL.. ........
{stkatg}  LTGEVKYTAT RADLVFGSSN VLRALAEVYA CSDAHEKFVK DFVAAWVKVM NLDRFDLQ.. ........
{bspera}  KTGEVRWTAT RVDLIFGSNS ILRSYAEFYA QDDNQEKFVR DFINAWVKVM NADRFDLVKK ARESVTA
{ccp}     .......... .......... .......... .......... .......... .......... ........
Consensus -TGEVKWTA- R-DLVFGSNS VLRALAEVYA -SDA-EKFVK DFVAAWVKVM NLDRFDL--- -------
```

NUCLEIC ACID PROBES, SEQUENCES AND METHODS FOR DETECTING *MYCOBACTERIUM TUBERCULOSIS* RESISTANT TO ISONIAZID

CROSS-REFERENCE TO RELATED APPLICATIONS

This application is a continuation-in-part of application Ser. No. 07/929,206, filed Aug. 14, 1992 (Atty. Docket No. 03495-0110-01) now U.S. Pat. No. 5,633,131, which is a continuation-in-part of application Ser. No. 07/875,940, filed Apr. 30, 1992 (now abandoned), and application Ser. No. 08/029,655, filed Mar. 11, 1993 (Atty. Docket No. 03495-0110-02000), abandoned, which is a continuation-in-part of application Ser. No. 07/875,940, filed Apr. 30, 1992 (now abandoned) and Ser. No. 07/929,206, filed Aug. 14, 1992. The entire disclosure of each of these applications is relied upon and incorporated by reference herein.

BACKGROUND OF THE INVENTION

This invention relates to the rapid detection of strains of *Mycobacterium tuberculosis* that are resistant to the antibiotic isoniazid. More particularly, this invention relates to a method of detecting isoniazid resistance in *Mycobacterium tuberculosis* by nucleic acid hybridization. This invention also relates to a nucleic acid probe and a kit for carrying out the nucleic acid hybridization.

Despite more than a century of research since the discovery of *Mycobacterium tuberculosis*, the aetiological agent of tuberculosis, by Robert Koch, this disease remains one of the major causes of human morbidity and mortality. There are an estimated 3 million deaths annually attributable to tuberculosis (Snider, 1989), and although the majority of these are in developing countries, the disease is assuming renewed importance in the West due to the increasing number of homeless people and the impact of the AIDS epidemic (Chaisson et al., 1987; Snider and Roper, 1992).

Isonicotinic acid hydrazide or isoniazid (INH) has been used in the treatment of tuberculosis for the last forty years due to its exquisite potency against the members of the "tuberculosis" groups—*Mycobacterium tuberculosis, M. bovis* and *M. africanum* (Middlebrook, 1952; Youatt, 1969). Neither the precise target of the drug, nor its mode of action, are known, and INH treatment results in the perturbation of several metabolic pathways. There is substantial evidence indicating that INH may act as an anti-metabolite of NAD and pyridoxal phosphate (Bekierkunst and Bricker, 1967; Sriprakash and Ramakrishnan, 1970; Winder and Collins, 1968, 1969, 1970), and other data indicating that the drug blocks the synthesis of the mycolic acids, which are responsible for the acid-fast character of mycobacterial cell walls (Winder and Collins 1970; Quemard et al., 1991). Shortly after its introduction, INH-resistant isolates of *Mycobacterium tuberculosis* emerged and, on characterization, were often found to have lost catalase-peroxidase activity and to show reduced virulence in guinea pigs (Middlebrook et al., 1954; Kubica et al., 1968; Sriprakash and Ramakrishnan, 1970).

Very recently, INH-resistance has acquired new significance owing to a tuberculosis epidemic in the USA due to multi-drug resistant (MDR) variants of *M. tuberculosis* (CDC, 1990; 1991a, b) and the demonstration that such strains were responsible for extensive nosocomial infections of HIV-infected individuals and health care workers (Snider and Roper, 1992). In view of the gravity of this problem, there exists a need in the art to determine the relationship between INH-resistance and catalase-peroxidase production.

More particularly, there is a need in the art to understand the molecular mechanisms involved in drug sensitivity. In addition, there is a need in the art to develop a simple test permitting the rapid identification of INH-resistant strains. Further, there is a need in the art for reagents to carry out such a test.

SUMMARY OF THE INVENTION

Accordingly, this invention aids in fulfilling these needs in the art by providing a process for detecting in vitro the presence of cells of a *Mycobacterium tuberculosis* resistant to isoniazid. The process comprises the steps of:

(A) depositing and fixing nucleic acids of the cells on a solid support, so as to make the nucleic acids accessible to a probe;

(B) contacting the fixed nucleic acids from step (A) with a probe under conditions permitting hybridization;

(C) washing the filter resulting from step (B), so as to eliminate any non-hybridized probe; and then (D) detecting any hybridized probe on the washed filter resulting from step (C).

The probe comprises a nucleic acid sequence which is present in a 2.5 kb EcoRV-KpnI fragment of plasmid pYZ55, wherein said fragment contains a BamHI cleavage site. This fragment has been found to be associated with intracellular DNA of isoniazid-sensitive *Mycobacterium tuberculosis* and is capable of distinguishing such antibiotic sensitive microorganisms from isoniazid-resistant *Mycobacterium tuberculosis*, which do not contain DNA that hybridizes with this fragment under the conditions described hereinafter.

This invention further provides nucleotide sequences, such as RNA and DNA, of isoniazid-resistant *Mycobacterium tuberculosis* encoding the region of the katG gene of *Mycobacterium tuberculosis* that imparts isoniazid sensitivity absent from isoniazid-resistant cells.

This invention also provides a probe consisting of a label, such as a radionuclide, bonded to a nucleotide sequence of the invention.

In addition, this invention provides a hybrid duplex molecule consisting essentially of a nucleotide sequence of the invention hydrogen bonded to a nucleotide sequence of complementary base sequence, such as DNA or RNA.

Also, this invention provides a process for selecting a nucleotide sequence coding for a catalase-peroxidase gene of *Mycobacterium tuberculosis,* or for a portion of such a nucleotide sequence, from a group of nucleotide sequences, which comprises the step of determining which of the nucleotide sequences hybridizes to a nucleotide sequence of the invention. The nucleotide sequence can be a DNA sequence or an RNA sequence. The process can include the step of detecting a label on the nucleotide sequence.

Further, this invention provides a kit for the detection of *Mycobacterium tuberculosis* resistant to isoniazid. The kit comprises a container means containing a probe comprising a nucleic acid sequence, which is a 2.5 kb EcoRV-KpnI fragment of plasmid pYZ55, wherein the fragment contains a BamHI cleavage site. The kit also includes a container means containing a control preparation of nucleic acid.

The invention also covers compounds obtained as products of the action of the enzyme catalase, or a similar enzyme on isoniazid. The katG gene or a derivative of this gene which retains a similar activity can be used as a source of catalase protein. The new compounds are selected by reactivity on INH-resistant-mycobacterial strains by the antibiogram method such as described in H. David et al.'s "Methodes de laboratoire pour Mycobacteriologie clinique" edited by Pasteur Institut, ISBN No. 0995-2454.

BRIEF DESCRIPTION OF THE DRAWINGS

This invention will be described in greater detail by reference to the drawings in which.

Restriction sites for the following enzymes are indicated: B, BamHl; C, Cal; E, EcoRV; H, Hindlll, K, Kpnl; M, Smal; N, Notl; R, EcoRl; S, Sacl. Transformation of BH1 with a mycobacterial shuttle plasmid, pBAK14 (Zhang et al., 1991), containing the 4.5 kb insert from pYZ55 similarly conferred INH-susceptibility. MIC's are also shown for BH1 transformed with subfragments derived from pYZ55 and inserted into pBAK14 in one (+) or other (–) orientation. The katG gene and the ability to confer INH-susceptibility both mapped to a 2.9 kb EcoRV-KpnI fragment (pBAK-KE+).

Figure 5:
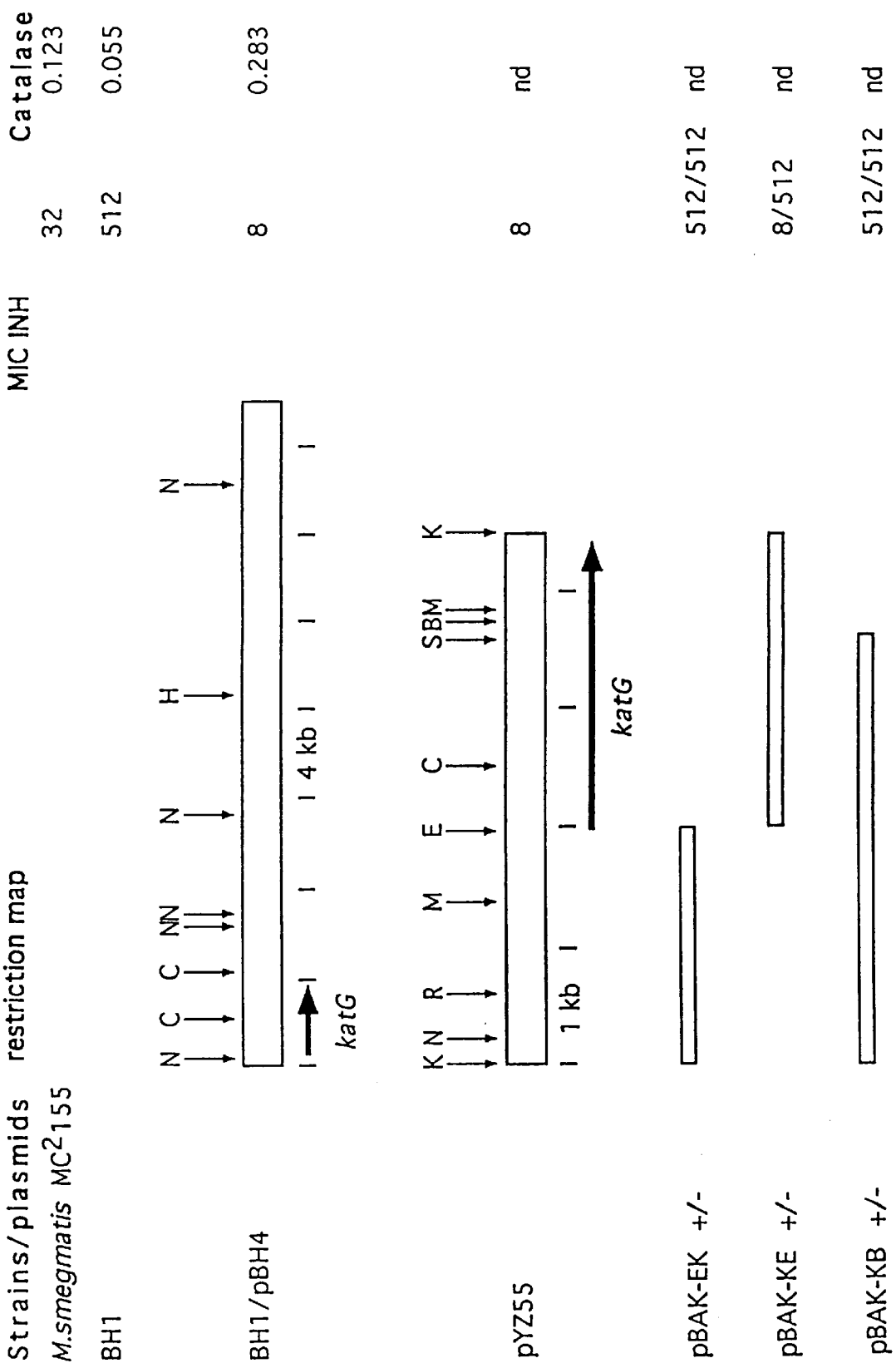
FIG. 5. shows the INH-resistant M. smegmatis strain, BH1 (Gayathri et al., 1975) (a derivative of strain mc$^2$-155[10]) was transformed with a pool of M. tuberculosis H37Rv shuttle cosmids (kindly provided by Dr. W. R. Jacobs, New York) and individual clones were scored for INH-susceptibility. Cosmid pBH4 consistently conferred drug susceptibility and the transformant overproduced catalase (assayed as in Heym). The restriction map of the DNA insert from pBH4 is shown along with that of the insert from pYZ55 —a plasmid containing katG of M. tuberculosis H37Rv, isolated on the basis of hybridization with an oligonucleotide probe (5'-TTCAT-CCGCATGGCCTGGCACGGCGCGGGCACCTACCGC-3'SEQ ID NO: 1) designed to match the amino acid sequence from a conserved region of E. coli HPI.
Figure 6A:
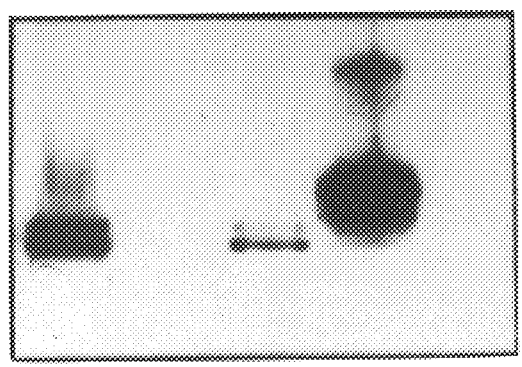
Figure 6B:
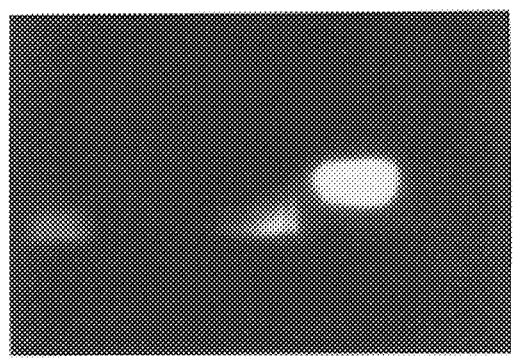

FIGS. 6A–C show extracts from M. tuberculosis H37Rv and from E. coli strains transformed with a variety of plasmid constructs that were prepared for activity gel analysis as described previously (zhang et al., 1991). Non-denaturing gels containing 8% polyacrylamide were stained for catalase (panel A) and peroxidase (panel B) activities as described by Wayne and Diaz (Wayne et al., 1986). Lane 1, M. tuberculosis H37Rv; 2, E. coli UM2 (katE, katG, ref. 15); 3, E. coli UM2/pYZ55; 4, E. coli UM2/pYZ56 (the 2.9 kb EcoRV-KpnI fragment in pUC19, corresponding to pBAK-KE+ in FIG. 1); 5, E. coli UM2/pYZ57 (pYZ55 with a BamHl-Kpnl deletion, corresponding to pBAK-KB+ in FIG. 5). M. tuberculosis catalase and peroxidase activities migrated as two bands under these conditions (lane 1); the same pattern was seen for the recombinant enzyme expressed by pYZ55 (lane 3). pYZ56 (lane 4) expresses a protein of increased molecular weight due to a fusion between katG and lacZ' from the vector as shown in panel C. Panels C(1) and C(2) also show partial sequence alignment with E. coli HPl (the complete sequence of the gene will be communicated elsewhere). In FIG. 6(c), the amino acid sequence for M. Tuberculosis is identified by SEQ ID NO:2, the nucleotide sequence is identified by SEQ ID NO:3, and the amino acid sequence for E. coli is identified by SEQ ID NO:4.

Figure 7:
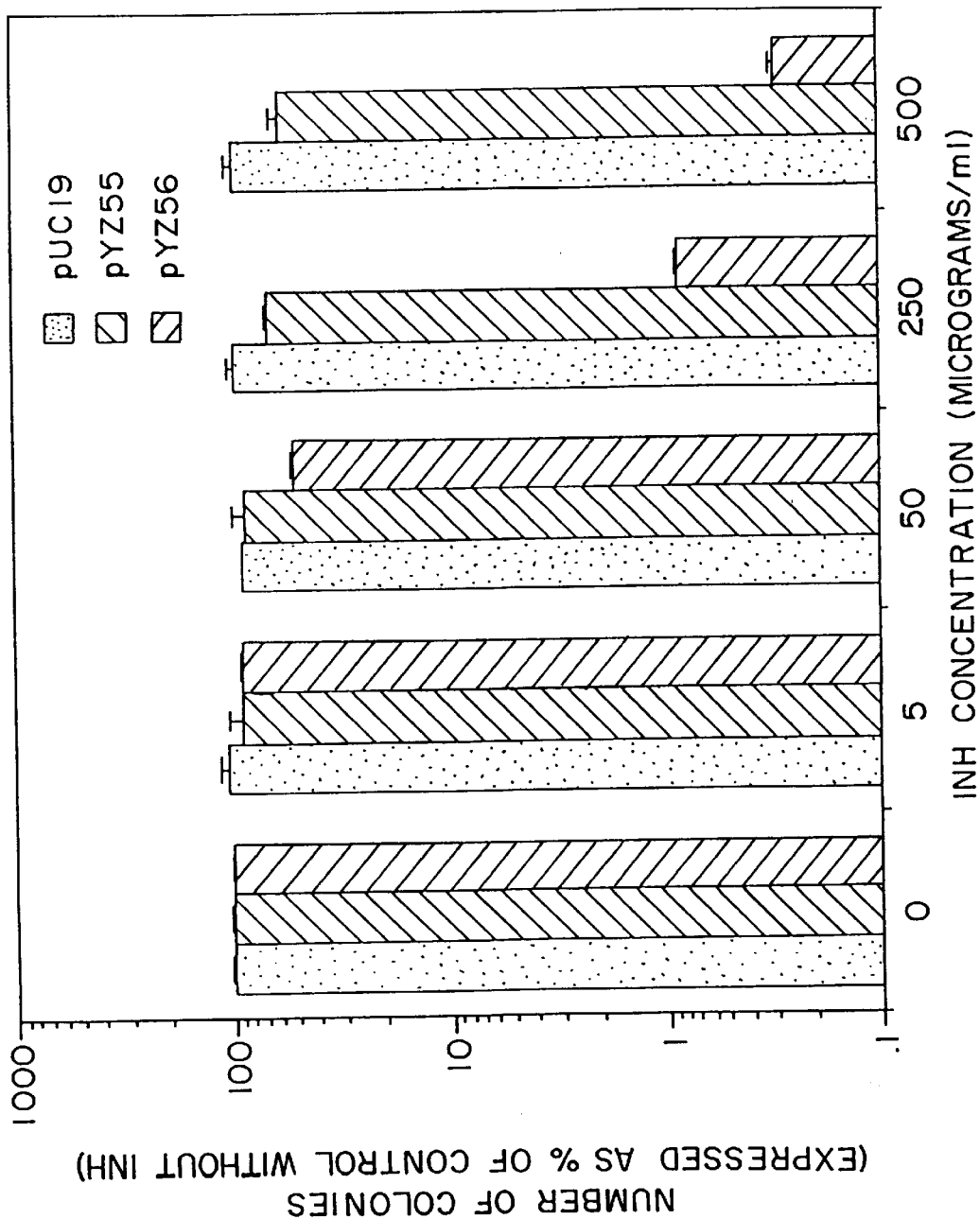

FIG. 7 shows an E. coli strain with mutations in both katG and katE (UM2, ref. 15) that was transformed with pUC19 vector alone (hatched bars), pYZ55 expressing M. tuberculosis katG (open bars) and pYZ56 with high level expression of M. tuberculosis katG (solid bars). Overnight cultures in Luria-Bertani broth supplemented with appropriate antibiotics were plated out in the presence of varying concentrations of INH and colony forming units were assessed. Results of a representative experiment are shown with error bars indicating the standard deviation observed in triplicate samples. Overexpression of M. tuberculosis katG similarly conferred susceptibility to high concentrations of INH in E. coli UM255 (katG, katE, Mulvey et al., 1988), but had no effect on catalase-positive strains such as E. coli TG1. In some experiments, high concentrations of INH had detectable inhibitory effect on growth of UM2 and UM255, alone, but in all experiments inhibition of pYZ56-transformants was at least 10–100 fold greater than that observed in the corresponding vector controls.

Figure 8A:
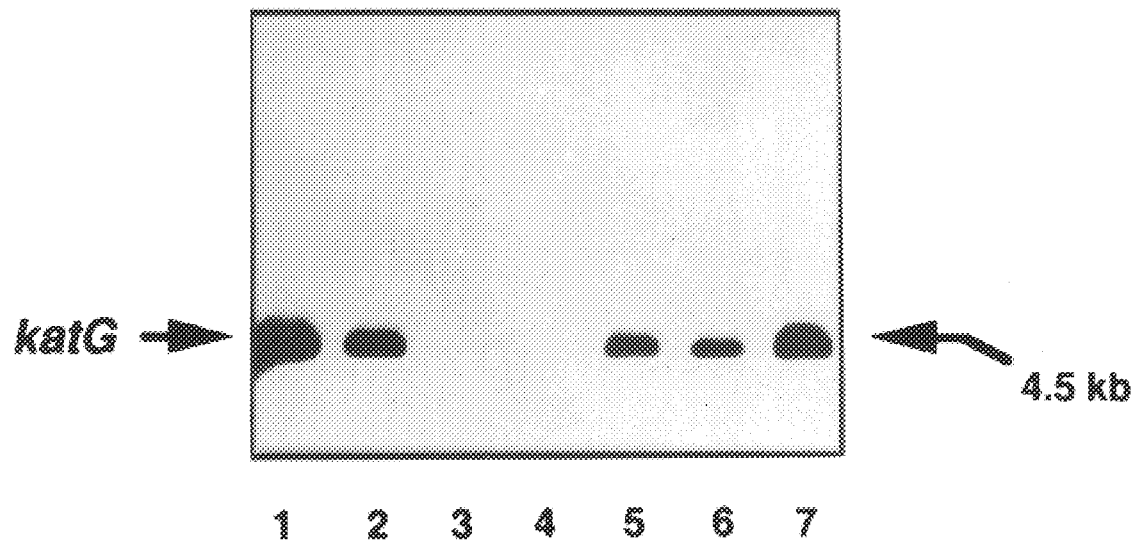
Figure 8B:
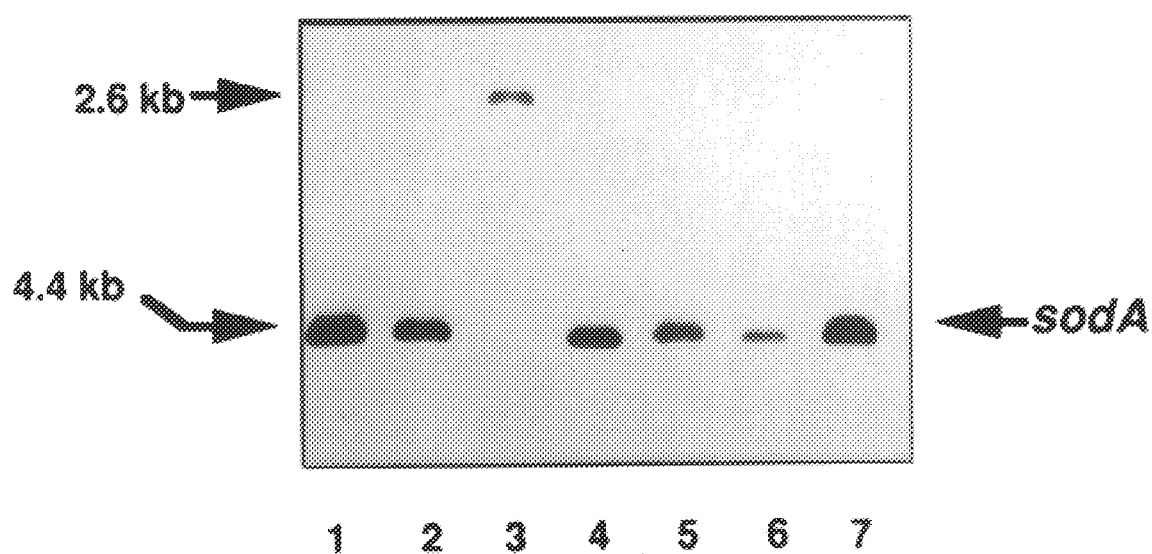

FIGS. 8A and B show Southern blots prepared using genomic DNA from different M. tuberculosis strains, digested with Kpn1, that were probed with (A) katG (the 4.5 kb Kpn1 fragment), and (B) the SOD gene (1.1 kb EcoRI-Kpn1 fragment, Zhang et al., 1991). Labelling of probes and processing of blots was performed as described previously (Quenard et al., 1991). Lane 1, H37Rv; 2, strain 12— MIC 1.6 μg/ml INH; 3, B1453—MIC>50 μg/ml INH (Jackett et al., 1978); 4, strain 24—MIC >50 μg/ml INH; 5, 79112—INH-sensitive (Mitchison et al., 1963); 6, 12646—INH-sensitive (Mitchison et al., 1963); 7, 79665—INH-sensitive (Mitchison et al., 1963). INH susceptibilities were confirmed by inoculation of Lowenstein-Jensen slopes containing differing concentrations of INH.

Figure 9:
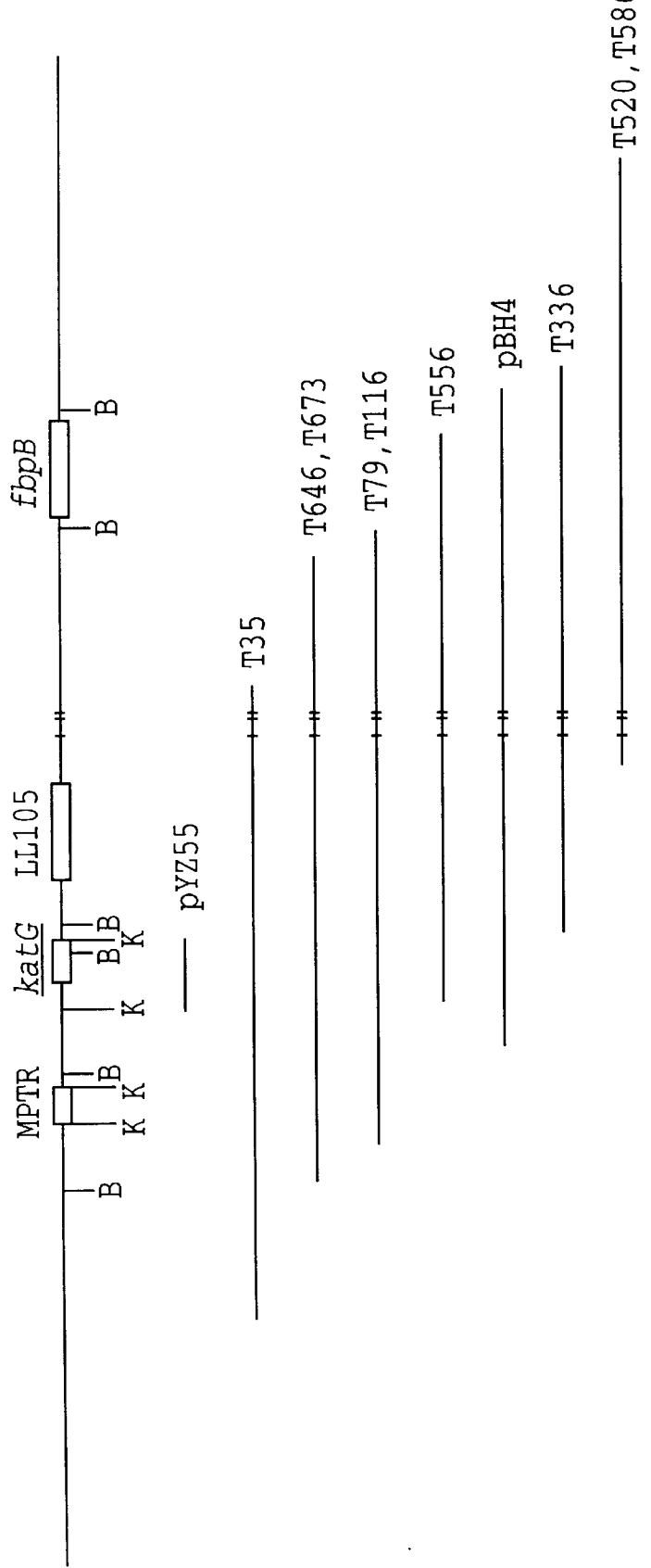

FIG. 9. Organization of the katG locus. The upper bar corresponds to a stretch of the M. tuberculosis chromosome spanning the katG region and the positions of individual cosmids used to construct the map are shown below together with the original shuttle cosmid pBH4 and pYZ55. The locations of some key restriction sites (B, BamHl; K, Kpnl) are shown together with the approximate location of the known genetic markers: fbpB encoding the alpha or 85-B antigen (Matsuo et al., 1988); katG, catalase-peroxidase; LL105, an anonymous λgt11 clone kindly supplied by Å Andersen; MPTR, major polymorphic tandem repeat (Hermans et al., 1992).

FIG. 10. A(1)–A(3). Nucleotide sequence of the KpnI fragment bearing katG (SEQ ID NO:8). This sequence has been deposited in the EMBL data-library under accession number X68081. The deduced protein sequence is shown in the one letter code(SEQ ID NO:9). FIG. B. Alignment of the two copies of the 700 bp direct repeat with identities shown as * and — denoting pads introduced to optimize the alignment (SEQ ID NO:10 and SEQ ID NO:11). Numbering refers to the positions in FIG. 6A.

Figure 11A:
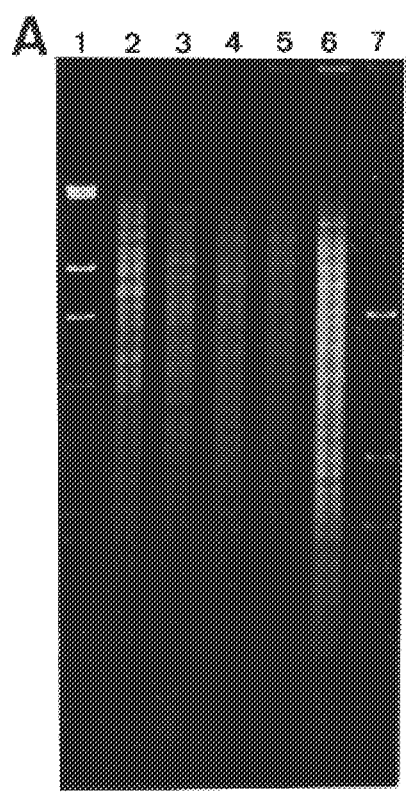
Figure 11B:
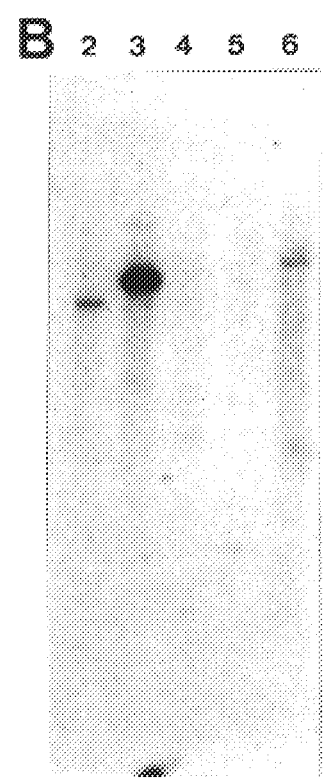

FIG. 11A and B. Distribution of katG in mycobacteria. A. Samples of different bacterial DNAs (1.5 µg) were digested with RsrII, separated by agarose gel electrophoresis and stained with ethidium bromide; lanes 1 and 7, size markers; *M. leprae*; lane 3, *M. tuberculosis* H37Rv; lane 4, *M. gordonae*; lane 5, *M. szulgai*; lane 6, *M. avium*. B. Hybridization of the gel in A, after Southern blotting, with a katG specific probe.

FIG. 12(1)–(2). Primary structure alignment of catalase-peroxidases. The sequences are from *M. tuberculosis* H37RV, mtkatg (SEQ ID NO:12); *E. coli*, eckatg (SEQ ID NO:13) (Triggs-Raine et al., 1988); *S. typhimurium*, stkatg (SEQ ID NO:14); *B. stearothermophilus*, bspera (SEQ ID NO:15) (Loprasert et al., 1988) and yeast cytochrome c peroxidase (SEQ ID NO:16) (ccp; Finzel et al., 1984). The alignment was generated using PILEUP and PRETTY (Devereux et al., 1984) and "." denotes gaps introduced to maximize the homology. Key residues from the active site and the peroxidase motifs (Welinder, 1991), discussed in the text, are indicated below the consensus (SEQ ID NO:17).

Figure 13:
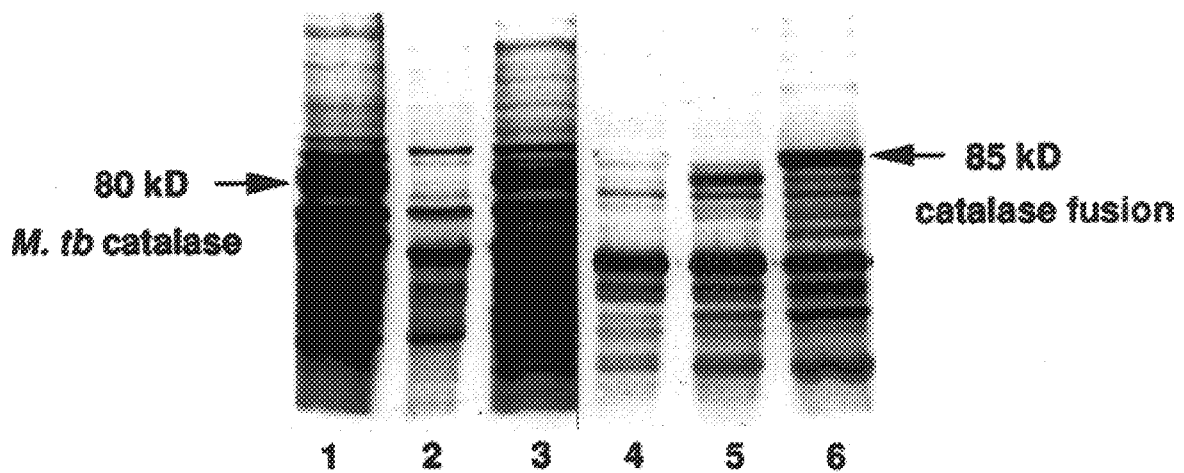

FIG. 13. Western blot analysis of *M. tuberculosis* KatG produced in different bacteria. Proteins were separated by SDS-polyacylamide gel electrophoresis then subjected to immuno-blotting, and detection with antiserum raised against BCG, as described in Zhang et al., 1991. Lane 1, soluble extract of *M. tuberculosis* H37Rv; lane 2, *M. smegmatis* MC²155 harboring the vector pBAK14; lane 3, MC²155 harboring pBAK-KK (katG⁺); lane 4, *E. coli* UM2 (katE, katG), lane 5, UM2 harboring pYZ55 (katG⁺); lane 6, UM2 harboring pYZ56 (lacZ'::katG).

DETAILED DESCRIPTION OF PREFERRED EMBODIMENT

The recent emergence of large numbers of strains of *M. tuberculosis* showing multi-drug resistance in the United States is a most alarming development given the extreme contagiousness of this organism. This danger has been strikingly illustrated by several small tuberculosis epidemics in which a single patient infected with MDR *M. tuberculosis* has infected both HIV-positive individuals, prison guards and healthy nursing staff (CDC 1990, 1991; Daley et al., 1992; Snider and Roper, 1992). Given the gravity of the current worldwide HIV epidemic, it is conceivable that if AIDS patients in the West, like those in Africa, were to be infected with MDR *M. tuberculosis* strains (rather than members of the *M. avium/M. intracellulare* complex) widespread dissemination of the disease would result.

Isoniazid (INH) is a bactericidal drug, which is particularly potent against the tuberculosis group of mycobacteria—*Mycobacterium tuberculosis, M. bovis,* and *M. africanum*—and, in consequence, it has been particularly effective in the treatment of tuberculosis. Standard anti-tuberculosis regimens generally include INH and rifampicin, often in combination with the weaker drugs, pyrazinamide, ethambutol or streptomycin. Besides its use in therapy INH is also given to close contacts of patients as a prophylactic measure.

INH-resistant mutants of *M. tuberculosis*, the agent of the human disease, show two levels of resistance: low (1 to 10 µg/ml) and high (10 to 100 µg/ml). INH-resistance is often associated with loss of catalase activity and virulence. Recently, owing to the AIDS epidemic, increased homelessness and declining social conditions, tuberculosis has re-emerged as a major public health problem in developed countries, particularly the USA. An alarming feature of the disease today is the emergence of multiple drug-resistant organisms and rapid nosocomial transmission to health care workers and HIV-infected patients. This has prompted CDC to propose new recommendations for the treatment of multiple resistant strains (at least INH and rifampicin) and the prevention of transmission. To obtain fresh insight into the problem of INH-resistance and to develop a rapid diagnostic test the following study was performed.

Clearly, it is essential to understand the mechanisms of resistance to INH and rifampicin, the main anti-tuberculosis agents, as this will allow novel chemotherapeutic strategies to be developed and facilitate the design of new compounds active against MDR strains.

This invention demonstrates that it is the catalase-peroxidase enzyme, HPI, which is the INH target, and it is suggested that this enzyme alone mediates toxicity. Compelling evidence of this conclusion was obtained by expression of the *M. tuberculosis* katG gene in a catalase-negative mutant of *E. coli* as this resulted in this bacterium becoming sensitive to INH. Moreover, the isolation of the *M. tuberculosis* INH-sensitivity gene, katG, is important as it will facilitate the rapid detection of INH-resistant strains by means of hybridization and PCR-based approaches. The high frequency of katG deletions in clinical strains, as shown here, should simplify this procedure.

Identification of an *M. tuberculosis* gene involved in INH-sensitivity

A heterologous approach was employed to isolate *M. tuberculosis* gene(s) involved in INH-sensitivity. BH1 is a spontaneous mutant of the easily transformable *M. smegmatis* strain MC²155 (Snapper et al., 1990), that is resistant to 512 µg/ml of the INH and lacks catalase-peroxidase activity (Heym et al., 1992). As there is a strict correlation between INH-sensitivity and these enzyme activities, transformation of BH1 with a plasmid carrying the appropriate gene from *M. tuberculosis* should lead to their restoration and concomitant INH-sensitivity.

Consequently, DNA was prepared from a pool of *M. tuberculosis* shuttle cosmids in *Escherichia coli* and introduced into BH1 by electro-transformation. Over 1000 kanamycin-resistant transformants were then scored for INH-sensitivity, and four clones that failed to grow on medium containing 32 g/ml of INH, the MIC from wild type strain MC²155, were obtained.

After re-transformation of BH1, only one of these, pBH4, consistently conferred the INH-sensitive phenotype. Restriction digests with BamHI, KpnI, NotI, ClaI and HindIII showed the *M. tuberculosis* chromosomal DNA carried by pBH4 to be about 30 kb in size. A map produced with the last three enzymes is presented in FIG. 1.

When pBH4 was used as a hybridization probe to detect homologous clones in the library, a further eight shuttle cosmids were isolated. On transformation into BH1, five of these (T35, T646, T673, T79, T556) restored INH-sensitivity, and showed similar restriction profiles to pBH4 (data not shown). In particular, a KpnI fragment of 4.5 kb was present in all cases.

Attempts to subclone individual BamHI fragments did not give rise to transformants capable of complementing the lesion in BH1 suggesting that a BamHI site might be located in the gene of interest. In contrast, pBH5, a derivative of pBH4, was constructed by deletion of EcoRI fragments and this showed that a 7 kb segment was not required for restoration of INH-sensitivity.

Transformants harboring shuttle cosmids that complemented the INH-resistant mutation of BH1 were examined carefully and the MICs for several antibiotics were established. In all cases, the MIC for INH had been reduced from 512 to 8 µg/ml, a value lower than that of the sensitive strain $MC^2$ 155 (32 µg/ml). This hypersensitive phenotype suggested that the recombinant clones might be overproducing an enzyme capable of enhancing INH-toxicity. Enzymological studies showed that these transformants all produced about 2-fold more peroxidase and catalase than the wild type strain $MC^2155$, which is INH-sensitive (data not shown).

In addition to INH, many MDR-strains of M. tuberculosis are no longer sensitive to rifampicin, streptomycin, ethambutol and pyrazinamide. To examine the possibility that there might be a relationship between resistance to INH and these compounds, the MICs of several drugs for various M. smegmatis strains and their pBH4 transformants were determined, but no differences were found.

Cloning the M. tuberculosis catalase gene

A 45-mer oligonucleotide probe was designed based on the primary sequences of highly conserved regions in the catalase-peroxidase enzymes, HPI, of E. coli (Triggs-Raine et al., 1989), and Bacillus stearothermophilus (Loprasert et al., 1988). When genomic blots of M. tuberculosis DNA were probed with this oligonucleotide, specific bands were detected in most cases. As KpnI generated a unique fragment of 4.5 kb that hybridized strongly, this enzyme was used to produce a size selected library in pUC19.

Upon screening with the oligonucleotide probe, an appropriate clone, pYZ55, was obtained. A restriction map of the insert DNA is presented in FIG. 1 where it can be seen that this corresponds exactly to part of pBH4. Independent confirmation was also obtained by cross-hybridization.

By means of various subcloning experiments the smallest fragment expressing M. tuberculosis catalase-peroxidase activity in E. coli was found to be a 2.5 kb EcoRV-KpnI fragment which, as expected, contained a cleavage site for BamHI. Partial DNA sequence analysis showed that the katG gene carried by pYZ55 encodes a catalase-peroxidase enzyme that is highly homologous to the HPI enzymes of E. coli and B. stearothermophilus:

(lane 1) which comigrated with catalase activity (data not shown; Heym et al., 1992).

When introduced into E. coli, the katG gene directed the synthesis of the same proteins, whereas pYZ56 produced proteins slightly larger in size. This is due to the construction of an in-frame lacZ::katG gene fusion. Activity stains were also performed with cell extracts of M. smegmatis. The presence of the katG gene from the M. tuberculosis in BH1 led to the production of catalase-peroxidase enzyme, which displayed the same electrophoretic mobility as the enzyme made in M. tuberculosis, or in E. coli, and the native HPI of M. smegmatis.

Basis of INH-resistance in M. tuberculosis

Figure 3:
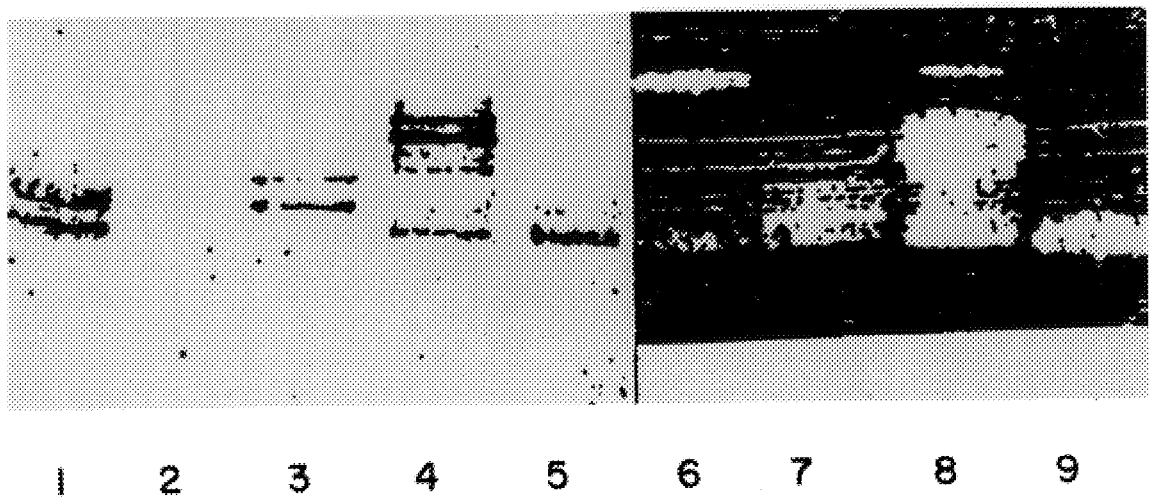
FIG. 3 shows the detection of recombinant M. tuberculosis catalase/peroxidase by activity staining. Cell extracts were separated by polyacrylamide gel electrophoresis and stained for peroxidase (lanes 1–5) and catalase activity. Samples were from M. tuberculosis, lane 1; E. coli TG1, lanes 2, 6; TG1/pYZ55 (katG+), lanes 3 and 7; TG1/pBAK16 (lacZ'::katG), lanes 4 and 8; TG1/pYZ78 (=pYZ55 deleted of 1.4 kb BamHI-KpnI fragment).
Figure 4A:
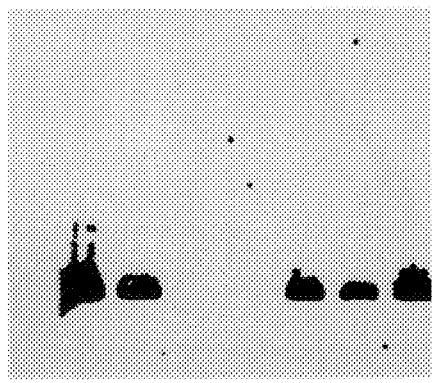
FIGS. 4A and 4B show the results of Southern blotting analysis of various M. tuberculosis strains using a 4.5 kb KpnI fragment as a probe. (A) Genomic DNA, digested with KpnI, was from strains H37Rv, lane 1; strain 12, lane 2; B1453, lane 3; strain 24, lane 4; 79112, lane 5; 12646, lane 6; 79665, lane 7. Strains B1453 and 24 are resistant to high levels of INH, strain 12 to low levels while the others are INH-sensitive. (B) As a control, the same blot was hybridized with a probe for the sodA gene (Zhang et al., 1991). Note the IS6110-mediated polymorphism associated with B1453.
Figure 4B:
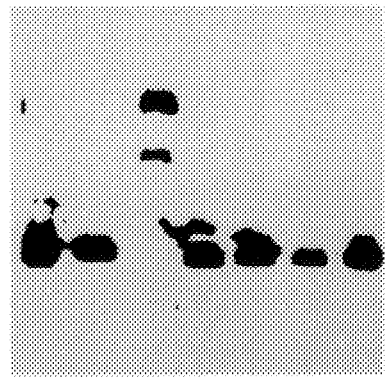

It has been known for many years that a subset of INH-resistant strains, particularly those resistant to the highest drug concentrations, are of lower virulence in the guinea pig and devoid of catalase activity. Genomic DNA was prepared from several clinical isolates of M. tuberculosis and analyzed by Southern blotting using the 4.5 kb KpnI fragment as a probe. In two highly resistant strains, B1453 and 24, the catalase gene has been deleted from the chromosome whereas in others (FIG. 3), such as strain 12, showing low level resistance it is still present but not expressed. Additional studies showed that the region immediately prior to katG was highly prone to rearrangements (data not shown).

M. tuberculosis HPI renders E. coli sensitive to INH

To determine whether the HPI enzyme of M. tuberculosis could confer INH sensitivity on E. coli, a series of catalase mutants was transformed with pYZ56 and the MICs determined. Wild type strains were not susceptible to INH, but mutants lacking both endogenous catalase activities, but harboring PYZ56, showed growth inhibition when high levels of INH (500 µg/ml) were present, whereas untransformed strains were insensitive.

For purposes of this invention, plasmid containing the restriction endonuclease map shown in FIG. 5 was deposited in strain with the National Collection of Cultures of Microorganisms (C.N.C.M.) of the Institut Pasteur, in Paris,

| M. tuberculosis | A P L N S WP D N A S L D K A R R L L WP S K K K Y G K K L S WA D L I V (SEQ ID NO: 5) |
|---|---|
| E. coli | * * * * * * * * * V * * * * * * * * * * I * Q * * * Q * I * * * * * F I (SEQ ID NO: 6) |
| B. stearothermophilus | * * * * * * * * * * N * * * * * * C * G R * * R N T * T * – * L G P I C S (SEQ ID NO: 7) |

Figures 1, 2:
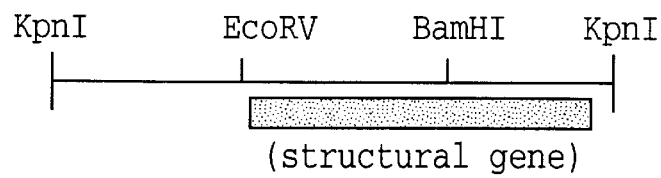
FIG. 1 is a restriction map of an insert present in pYZ55 showing the location of katG.
FIG. 2 is a partial sequence of the M. tuberculosis catalase/peroxidase polypeptide and comparison with the HPI enzymes from E. coli and B. stearothermophilus. Identical residues are indicated by *.

(FIG. 2; Triggs-Raine et al., 1988); (Loprasert et al., 1988). Identical residues are indicated by *. HPI activity was detected in both E. coli and M. smegmatis by staining (see below).

Catalase-peroxidase involvement in INN-sensitivity

Having cloned the M. tuberculosis katG gene, it was of immediate interest to investigate the genetic basis of the association between catalase-negativity and isoniazid resistance. A series of constructs was established in the shuttle vector pBAK14 and used to transform the INH-resistant M. smegmatis mutant BH1. Only those plasmids carrying a complete katG gene produced HPI and restored INH-sensitivity. The smallest of these, pBAK16, carried a 2.5 kb EcoRV-KpnI fragment thus demonstrating that the 2 kb region upstream of katG was not involved, and that catalase-peroxidase activity alone was sufficient to render mycobacteria susceptible to INH.

Cell-free extracts were separated by non-denaturating polyacrylamide gel electrophoresis and stained for peroxidase and catalase activity. Under these conditions, the M. tuberculosis enzyme gave two bands of peroxidase activity France on May 18, 1992, under culture collection accession No. I-1209. This plasmid contains the nucleic acid sequence of the invention, namely, the 4.5 kb KpnI-KpnI fragment of plasmid pYZ55 having the BamHI cleavage site in the fragment.

In general, the invention features a method of detecting the presence of isoniazid-resistant Mycobacterium tuberculosis in a sample including providing at least one DNA or RNA probe capable of selectively hybridizing to isoniazid-sensitive Mycobacterium tuberculosis DNA to form detectable complexes. Detection is carried out with a sample under conditions which allow the probe to hybridize to isoniazid-sensitive Mycobacterium tuberculosis DNA present in the sample to form hybrid complexes and detecting the hybrid complexes as an indication of the presence of isoniazid-sensitive Mycobacterium tuberculosis in the sample. (The term "selectively hybridizing", as used herein, refers to a DNA or RNA probe which hybridizes only to isoniazid-sensitive Mycobacterium tuberculosis and not to isoniazid-sensitive Mycobacterium tuberculosis.) The sample can be comprised of the Mycobacterium tuberculosis cells or a portion of the cells or cell contents enriched in *Mycobacterium tuberculosis* nucleic acids, especially DNA. Hybridization can be carried out using conventional hybridization reagents. The particular hybridization conditions have not been found to be critical to the invention.

More particularly, DNA sequences from *Mycobacterium tuberculosis* can be analyzed by Southern blotting and hybridization. The techniques used for the present invention are described in Maniatis, Sambrook et al., (Cold Spring Harbor, Second Edition, 1989). DNA fragments can be separated on agarose gels and denatured in situ. The fragments can then be transferred from the gel to a water insoluble solid, porous support, such as a nitrocellulose filter, a nylon membrane, or an activated cellulose paper, where they are immobilized for example, the Hybond® membrane commercialized by Amersham are used. After prehybridization to reduce non-specific hybridization with the probe, the solid support is hybridized to the nucleic acid probe of the invention. The solid support is washed to remove unbound and weakly binding probe, and the resulting hybrid duplex molecule is examined. A convenient alternative approach is to hybridize oligonucleotides to the DNA denatured in the gel.

The amount of labeled probe which is present in the hybridization solution will vary widely, depending upon the nature of the label, the amount of the labeled probe which can reasonably bind to the filter, and the stringency of the hybridization. Generally, substantial excesses of the probe over stoichiometric will be employed to enhance the rate of binding of the probe to the fixed DNA.

Various degrees of stringency of hybridization can be employed. The more severe the conditions, the greater the complementarity that is required for hybridization between the probe and the polynucleotide for duplex formation. Severity can be controlled by temperature, probe concentration, probe length, ionic strength, time, and the like. Conveniently, the stringency of hybridization is varied by changing the polarity of the reactant solution. Temperatures to be employed can be empirically determined or determined from well known formulas developed for this purpose.

Unlike Southern hybridization where DNA fragments are transferred from an agarose gel to a solid support, the method of the invention can also be carried out by oligonucleotide hybridization in dried agarose gels. In this procedure, the agarose gel is dried and hybridization is carried out in situ using an oligonucleotide probe of the invention. This procedure is preferred where speed of detection and sensitivity may be desirable. The procedure can be carried out on agarose gels containing genomic or cloned DNA of *Mycobacterium tuberculosis*.

In addition, the method of this invention can be carried out by transfer of *Mycobacterium tuberculosis* DNA from polyacrylamide gels to nylon filters by electroblotting. Electroblotting may be desirable where time is of the essence, because electroblotting is typically faster than capillary blotting developed to transfer DNA from agarose gels. This method can be carried out in conjunction with UV-crosslinking. The polyacrylamide gel containing the samples to be tested is placed in contact with an appropriately prepared nylon filter. These are then sandwiched into an electroblotting apparatus and the DNA is transferred from the gel onto the filter using electric current. After a buffer rinse, the filter is ready to be prehybridized and hybridized or UV-crosslinked.

The method of the invention can be carried out using the nucleic acid probe of the invention for detecting *Mycobacterium tuberculosis* resistant to isoniazid. The probe can be detected using conventional techniques.

The nucleotides of the invention can be used as probes for the detection of a nucleotide sequence in a biological sample of *M. tuberculosis*. The polynucleotide probe can be labeled with an atom or inorganic radical, most commonly using a radionuclide, but also perhaps with a heavy metal. Radioactive labels include $^{32}P$, $^{3}H$, $^{14}C$, or the like. Any radioactive label can be employed, which provides for an adequate signal and has sufficient half-life. Other labels include ligands that can serve as a specific binding member to a labeled antibody, fluorescers, chemiluminscers, enzymes, antibodies which can serve as a specific binding pair member for a labeled ligand, and the like. The choice of the label will be governed by the effect of the label on the rate of hybridization and binding of the probe to the DNA or RNA. It will be necessary that the label provide sufficient sensitivity to detect the amount of DNA or RNA available for hybridization.

In preferred embodiments of the invention, the probe is labeled with a radioactive isotope, e.g., $^{32}P$ or $^{125}I$, which can be incorporated into the probe, e.g., by nick-translation.

In other preferred embodiments, the probe is labeled with biotin, which reacts with avidin to which is bonded a chemical entity which, when the avidin is bonded to the biotin, renders the hybrid DNA complex capable of being detected, e.g., a fluorophore, which renders the hybrid DNA complex detectable fluormetrically; an electron-dense compound capable of rendering the hybrid DNA complexes detectable by an electron microscope; an antibody capable of rendering the hybrid DNA complexes immunologically detectable; or one of a catalyst/substrate pair capable of rendering the hybrid DNA complexes enzymatically detectable. Prior to contacting the bacteria with the probe, the *M. tuberculosis* bacteria can be lysed to release their DNA, which is then denatured and immobilized on an appropriate solid, DNA-binding support, such as a nitrocellulose membrane.

Another detection method, which does not require the labeling of the probe, is the so-called sandwich hybridization technique. In this assay, an unlabeled probe, contained in a single-stranded vector, hybridizes to isoniazid-sensitive *Mycobacterium tuberculosis* DNA, and a labeled, single-stranded vector, not containing the probe, hybridizes to the probe-containing vector, labeling the whole hybrid complex.

The sequences of the invention were derived by dideoxynucleotide sequencing. The base sequences of the nucleotides in are written in the 5'----->3' direction. Each of the letters shown is a conventional designation for the following nucleotides:

| | |
|---|---|
| A | Adenine |
| G | Guanine |
| T | Thymine |
| C | Cytosine. |

The nucleotides of the invention can be prepared by the formation of 3'→5' phosphate linkages between nucleoside units using conventional chemical synthesis techniques. For example, the well-known phosphodiester, phosphotriester, and phosphite triester techniques, as well as known modifications of these approaches, can be employed. Deoxyribonucleotides can be prepared with automatic synthesis machines, such as those based on the phosphoramidite approach. Oligo- and polyribonucleotides can also be obtained with the aid of RNA ligase using conventional techniques.

The nucleotides of the invention are in a purified form. For instance, the nucleotides are free of human blood-derived proteins, human serum proteins, viral proteins, nucleotide sequences encoding these proteins, human tissue, and human tissue components. In addition, it is preferred that the nucleotides are free of other nucleic acids, extraneous proteins and lipids, and adventitious microorganisms, such as bacteria and viruses.

This invention of course includes variants of the nucleotide sequences of the invention or serotypic variants of the probes of the invention exhibiting the same selective hybridization properties as the probes identical herein.

The nucleotide sequences of the present invention can be employed in a DNA amplification process known as the polymerase chain reaction (PCR). See. e.g., S. Kwok et al., J. Virol., 61:1690–1694 (1987). PCR is advantageous because this technique is rapid.

DNA primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the PBMC DNA. The PCR reaction mixture can contain the PBMC DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the PBMC DNA at an elevated temperature, cooling of the reaction mixture, and polymerization with the DNA polymerase.

Amplified sequences can be detected by the use of a technique termed oligomer restriction (OR). See, R. K. Saiki et al., Bio/Technology 3:1008–1012 (1985) and SSCP PNAS 1989, vol. 86, p. 2766–2770. For example, after amplification, a portion of the PCR reaction mixture can be separated and subjected to hybridization with an end-labeled nucleotide probe, such as a $^{32}p$ labeled adenosine triphosphate end-labeled probe. In OR, an end-labeled oligonucleotide probe hybridizes in solution to a region of the amplified sequence and, in the process, reconstitutes a specific endonuclease site. Thus, hybridization of the labeled probe with the amplified katG sequence yields a double-stranded DNA form that is sensitive to selective restriction enzyme digestion. After restriction with an endonuclease, the resulting samples can be analyzed on a polyacrylamide gel, and autoradiograms of the portion of the gel with the diagnostic labeled fragment can be obtained. The appearance of a diagnostic fragment (e.g., 10–15 bases in length) in the autoradiogram indicates the presence of katG sequences in the PBMCs.

Since it may be possible to increase the sensitivity of detection by using RNA instead of chromosomal DNA as the original template, this invention contemplates using RNA sequences that are complementary to the DNA sequences described herein. The RNA can be converted to complementary DNA with reverse transcriptase and then subjected to DNA amplification.

EXPERIMENTAL PROCEDURES

Bacterial strains and plasmids

Table 1 outlines the properties of the bacterial strains and plasmids used in this invention.

TABLE 1

Bacterial Strains And Plasmids

| Strains/plasmids | Characteristics |
| --- | --- |
| E. coli NM554 | |
| E. coli TG1 | supE hsd5 thi delta (lac-proAB) [traD36 proAB+ lacI$^q$ lacZ delta M15] |
| E. coli UM2 | KatE |
| E. coli UM255 | KatE |
| M. tuberculosis H37RV | Virulent strain originally isolated from tuberculosis patient |
| M. tuberculosis 12 | Clinical isolate resistant to low levels of INH (1–2 μg/ml) |
| M. tuberculosis B1453 | Clinical isolate resistant to high levels of INH (>50 μg/ml) |
| M. tuberculosis 24 | Clinical isolate resistant to high levels of INH (>50 μg/ml) |
| M. tuberculosis 79112 | Clinical isolate sensitive to INH |
| M. tuberculosis 12646 | Clinical isolate sensitive to INH |
| M. tuberculosis 79665 | Clinical isolate sensitive to INH |
| M. smegmatis MC$^2$155 | MC$^2$6 het |
| M. smegmatis BH1 | MC$^2$155 het katG |
| Plasmids | |
| pBH4 | Shuttle cosmid, kat$^{G+}$, based on pYUB18 |
| pBH5 | Deleted version of pBH4, kat$^{G+}$, (7 kb-EcoRI) |
| pYZ55 | pUC19 derivative with 4.5 kb KpnI fragment, kat+ |
| pYZ56 | pUC19 derivative with 2.5 kb EcoRV-KpnI fragment (kat+) |
| PYZ57 | pUC19 derivative with 3.1 kb KpnI-BamHI fragment, kat− |
| pBAK14 | Mycobacterial shuttle vector (Zhang et al., 1991) |
| pBAK15 | Mycobacterial shuttle vector carrying 4.5 kb KpnI fragment (kat+) |
| pBAK16 | Mycobacterial shuttle vector carrying 2.5 kb EcoRV-KpnI fragment (kat$^+$) |
| PBAK17 | Mycobacterial shuttle vector carrying 3.1 kb KpnI-BamHI fragment (kat−) |

The M. tuberculosis H37 RV genomic library was constructed in the shuttle cosmid pYUB18 (Snapper et al., 1988) and kindly supplied by Dr. W. R. Jacobs. Other shuttle vectors employed were pYUB12 (Snapper et al., 1988) and pBAK14 (Zhang et al., 1991).

Microbiological techniques and enzymology

Details of antibiotics used, growth conditions, enzymology and MIC determinations can be found in Heym et al., (1992).

Nucleic acid techniques

Standard protocols were used for subcloning, Southern blotting, DNA sequencing, oligonucleotide biosynthesis, etc. (Maniatis et al., 1989; Eiglmeier et al., 1991).

Activity staining

The preparation of cell-free extracts of E. coli and mycobacteria has been described recently (Heym et al., 1992; Zhang et al., 1991). Native protein samples were separated by polyacrylamide gel electrophoresis as described by Laemmli (1970) except that SDS was omitted from all buffers, samples were not boiled and betamercaptoethanol was not included in the sample buffer. After electrophoresis of 50–100 μg protein samples on 7.5% polyacrylamide gels, catalase activity was detected by soaking the gel in 3 mM $H_2O_2$ for 20 minutes with gentle shaking. An equal volume of 2% ferric chloride and 2% potassium ferricyanide was added and clear bands of catalase activity revealed by illumination with light. Peroxidase activity was detected as brown bands after soaking gels in a solution containing 0.2–0.5 mg/ml diaminobenzidine and 1.5 mM $H_2O_2$ for 30–120 minutes.

To generate a highly toxic compound it seems most likely that the *M. tuberculosis* HPI enzyme peroxidatively activates INH (Youatt, 1969; Gayathri-Devi et al., 1975). Now that the katG gene has been isolated and characterized, it should be possible to make new derivatives of INH, which can be activated in a similar manner.

REFERENCES CITED IN SPECIFICATION

Bekierkunst, A. & Bricker, A. (1967). Studies on the mode of action of isoniazid on mycobacteria. *Arch. Biochem. Biophys.* 122:385–392.

C.D.C. Outbreak of multidrug-resistant tuberculosis—Texas, California, and Pennsylvania. MMWR 1990(b), 39:369–372.

C.D.C. Nosocomial transmission of multidrug-resistant tuberculosis among HIV-infected persons—Florida and New York 1988–1991. MMWR 1991(a) 40:585–591.

C.D.C. Transmission of multidrug-resistant tuberculosis from an HIV-positive client in a residential substance abuse treatment facility. Michigan. MMWR 1991(b), 40:129-131.

Chaisson, R. E., Schecter, G. F., Theuer, C. P., Rutherford, G. W., Echenberg, D. F., Hopewell, P. C. (1987). Tuberculosis in patients with the acquired immunodeficiency syndrome. *Am. Rev. Respir. Dis.,* 23:56–74.

Daley, C. L., Small, P. M., Schecter, G. F., Schoolnik, G. K., McAdam, R. A., Jacobs, W. R., and Hopewell, P. C. (1992). An outbreak of tuberculosis with accelerated progression among persons infected with the human immunodeficiency virus. An analysis using restriction-fragment-length-polymorphism. *N. Engl. J. Med.,* 326:231–235.

Devereux, J., Haeberli, P. and Smithies, O. (1984) A comprehensive set of sequence analysis programs for the VAX. Nucl Acids Res 12:387–395.

Eiglmeier, K., Honore, N., and Cole, S. T. (1991). Towards the integration of foreign DNA into the chromosome of *Mycobacterium leprae. Research in Microbiology,* 142:617–622.

Finzel, B. C., Poulos, T. L. and Kraut, J. (1984). Crystal structure of yeast cytochrome c peroxidase at 1.7 Å resolution. J. Biol. Chem. 259:13027–13036.

Gayathri Devi, B., Shaila, M. S., Ramakrishnan, T., and Gopinathan, K. P. (1975). The purification and properties of peroxidase in *Mycobacterium tuberculosis* H37RV and its possible role in the mechanism of action of isonicotinic acid hydrazide. *Biochem. J.,* 149:187–197.

Hermans, P. W. M., van Soolingen, D. and van Embden, J. D. A. (1992). Characterization of a major polymorphic tandem repeat in *Mycobacterium tuberculosis* and its potential use in the epidemiology of *Mycobacterium kansasii* and *Mycobacterium Ågordonae.* J. Bacteriol. 174:4157–4165.

Heym, B. and Cole, S. T. (1992). Isolation and characterization of isoniazid-resistant mutants of *Mycobacterium smegmatis* and *M. aurum. Res. Microbiol.,* submitted.

Jackett, P. S., Aber, V. and Lowrie, D. (1978). *J. Gen Microbiol.,* 104:37–45.

Kubica, G. P., Jones Jr., W. D., Abbott, V. D., Beam, R. E., Kilburn, J. O., and Cater Jr., J. C. (1966). Differential identification of mycobacteria. I. Tests on catalase activity. *Am. Rev. Resp. Dis.,* 94:400–405.

Laemmli, U. K., (1970). Cleavage of structural proteins during the assembly of the head of bacteriophage-T4. *Nature* (London) 227:680–685.

Loprasert, S., Negoro, S. and Okada, H. (1988). Thermostable peroxidase from *Bacillus stearothermophilus.* J. Gen Microbiol. 134:1971–1976.

Loprasert, S., Negoro, S., and Okada, H. (1989). Cloning, nucleotide sequence, and expression in *Escherichia coli* of the *Bacillus stearotherrrmophilus* peroxidase gene (perA). *J. Bacteriol.,* 171:4871–4875.

Maniatis, T., Sambrook, J., and Fritsch, E. F. (1989). Molecular cloning. A laboratory manual. Second Edition 1989. Cold Spring Harbor Laboratory Press.

Matsuo, K., Yamaguchi, R., Yamazaki, R. A., Tasaka, H. and Yamada, T. (1988). Cloning and expression of the *Mycobacterium bovis* BCG gene for extracellular α antigen. J. Bacteriol. 170:3847–3854.

Middlebrook, G. (1954). Isoniazid-resistance and catalase activity of tubercle bacilli. *Am. Rev. Tuberc.,* 69:471–472.

Middlebrook, G., Cohn, M. L., and Schaefer, W. B. (1954). Studies on isoniazid and tubercle bacilli. III. The isolation, drug-susceptibility, and catalase-testing of tubercle bacilli from isoniazid-treated patients. *Am. Rev. Tuberc.,* 70:852–872.

Mitchison, D. A., Selkon, J. B. and Lloyd, S. (1963). *J. Path. Bact.* 86:377–386.

Mulvey, M. R., Sorby P. A., Triggs-Raine B. L. and Loewen P. C. *Gene* 73:337–345 (1988).

Quemard, A., Lacave, C., and Laneelle, G. (1991). Isoniazid inhibition of mycolic acid synthesis by cell extracts of sensitive and resistant strains of *Mycobacterium aurum. Antimicrob. Ag. Chem.,* 35:1035–1039.

Snapper, S. B., Lugosi, L., Jekkel, A., Melton, R. E., Kieser, T., Bloom, B. R., and Jacobs, W. R. (1988). Lysogeny and transformation in mycobacteria: stable expression of foreign genes. *Proc. Natl. Acad. Sci. USA,* 85:6987–6991.

Snapper, S. B., Melton, R. E., Mustafa, S., Kieser, T., and Jacobs, W. R. (1990). Isolation and characterization of efficient plasmid transformation mutants of *Mycobacterium smegmatis. Mol. Microbiol.,* 4:1911–1919.

Snider, D. (1989). *Rev. Inf. Dis.*, S335.

Snider Jr., D. E. and Roper, W. L. (1992). The new tuberculosis. *The New England Journal of Medicine,* 326:703–705.

Sriprakash, K. S. and Ramakrishnan, T. (1970). Isoniazid-resistant mutants of *Mycobacterium tuberculosis* H37Rv: Uptake of isoniazid and the properties of NADase inhibitor. *J. Gen. Microbiol.,* 60:125–132.

Triggs-Raine, B. L., Doble, B. W., Mulvey, M. R., Sorby, P. A., and Loewen, P.C. (1988). Nucleotide sequence of kagG, encoding catalase HPI of *Escherichia coli. J. Bacteriol.,* 170:4415–4419.

Wayne, L. G. and Diaz, G. A. (1986). *Analyt. Biochem.* 157:89–92.

Welinder, K. G. (1991). Bacterial catalase-peroxidases are gene duplicated members of the plant peroxidase superfamily. Biochim. Biophys. Acta 1080:215–220.

Winder, F. and Collins, P. (1968). The effect of isoniazid on nicotinamide nucleotide levels in *Mycobacterium bovis,* strain BCG. *Amer. Rev. Respir. Dis.,* 97:719–720.

Winder, F. and Collins, P. (1968). The effect of isoniazid on nicotinamide nucleotide levels in *Mycobacterium bovis,* strain BCG. *Amer. Rev. Respir. Dis.,* 97:719–720.

Winder, F. and Collins, P. (1969). The effect of isoniazid on nicotinamide nucleotide concentrations in tubercle bacilli. *Amer. Rev. Respir. Dis.,* 100:101–103.

Winder, F. and Collins, P. (1968). Inhibition by isoniazid of synthesis of mycolic acids in *Mycobacterium tuberculosis, J. Gen. Microbiol.,* 63:41–48.

Youatt, J. (1969). A review of the action of isoniazid. *Am. Rev. Respir. Dis.,* 99:729–749.

Zhang, Y., Lathigra, R., Garbe, T., Catty, D., and Young, D. (1991) Genetic analysis of superoxide dismutase, the 23 kilodalton antigen of *Mycobacterium tuberculosis*. *Mol. Microbiol.*, 5:381–391.

---

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TTCATCCGCA  TGGCCTGGCA  CGGCGCGGGC  ACCTACCGC                    39
```

( 2 ) INFORMATION FOR SEQ ID NO:2:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Met Thr Met Ile Thr Pro Ser Leu His Ala Cys Arg Ser Thr Leu Glu
 1           5                  10                  15
Asp Pro His Pro Thr Leu Arg Asp His Ile Arg Asp His Ser Pro Ile
             20                  25                  30
Thr Pro Thr Pro Gly Arg Asn Ala Met Pro Glu Gln His Pro Pro Ile
             35                  40                  45
Thr Glu Thr Thr Thr Gly Ala Ala Ser Asn Gly Cys Pro Val Val Gly
     50                  55                  60
His Met Lys Tyr Pro Val Glu Gly Gly Gly Asn Gln Asp Trp Trp Pro
 65              70                  75                  80
Asn Arg Leu Asn Leu Lys Val Leu His Gln Asn Pro Ala Val Ala Asp
                 85                  90                  95
Pro Met Gly Ala Ala Phe Asp Tyr Ala Ala Glu Val Ala Thr Ser Arg
             100                 105                 110
Leu Asp Ala Leu Thr Arg Asp Ile
             115                 120
```

( 2 ) INFORMATION FOR SEQ ID NO:3:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
ATGACCATGA TTACGCCAAG CTTGCATGCC TGCAGGTCGA CTCTAGAGGA TCCCCATCCG    60
ACACTTCGCG ATCACATCCG TGATCACAGC CCGATAACAC CAACTCCTGG AAGGAATGCT   120
GTGCCCGAGC AACACCCACC CATTACAGAA ACCACCACCG GAGCCGCTAG CAACGGCTGT   180
```

CCCGTCGTGG GTCATATGAA ATACCCCGTC GAGGGCGGCG GAAACCAGGA CTGGTGGCCC 240

AACCGGCTCA ATCTGAAGGT ACTGCACCAA AACCCGGCCG TCGCTGACCC GATGGGTGCG 300

GCGTTCGACT ATGCCGCGGA GGTCGCGACC AGTCGACTTG ACGCCCTGAC GCGGGACATC 360

(2) INFORMATION FOR SEQ ID NO:4:

(i) SEQUENCE CHARACTERISTICS:
        (A) LENGTH: 78 amino acids
        (B) TYPE: amino acid
        (D) TOPOLOGY: linear (ii) MOLECULE TYPE: peptide (xi) SEQUENCE DESCRIPTION: SEQ ID NO:4:

Met Ser Thr Ser Asp Asp Ile His Asn Thr Thr Ala Thr Gly Lys Cys
1               5                   10                  15

Pro Phe His Gln Gly Gly His Asp Gln Ser Ala Gly Ala Gly Thr Thr
                20                  25                  30

Thr Arg Asp Trp Trp Pro Asn Gln Leu Arg Val Asp Leu Leu Asn Gln
            35                  40                  45

His Ser Asn Arg Ser Asn Pro Leu Gly Glu Asp Phe Asp Tyr Arg Lys
        50                  55                  60

Glu Phe Ser Lys Leu Asp Tyr Tyr Gly Leu Lys Lys Asp Leu
65                  70                  75

(2) INFORMATION FOR SEQ ID NO:5:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:5:

Ala Pro Leu Asn Ser Trp Pro Asp Asn Ala Ser Leu Asp Lys Ala Arg
1               5                   10                  15

Arg Leu Leu Trp Pro Ser Lys Lys Lys Tyr Gly Lys Lys Leu Ser Trp
                20                  25                  30

Ala Asp Leu Ile Val
            35

(2) INFORMATION FOR SEQ ID NO:6:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:6:

Ala Pro Leu Asn Ser Trp Pro Asp Asn Val Ser Leu Asp Lys Ala Arg
1               5                   10                  15

Arg Leu Leu Trp Pro Ile Lys Gln Lys Tyr Gly Gln Lys Ile Ser Trp
                20                  25                  30

Ala Asp Leu Phe Ile
            35

(2) INFORMATION FOR SEQ ID NO:7:

(i) SEQUENCE CHARACTERISTICS:
        (A) LENGTH: 36 amino acids

-continued ( B ) TYPE: amino acid
  ( D ) TOPOLOGY: linear ( i i ) MOLECULE TYPE: peptide ( x i ) SEQUENCE DESCRIPTION: SEQ ID NO:7:

```
Ala  Pro  Leu  Asn  Ser  Trp  Pro  Asp  Asn  Ala  Asn  Leu  Asp  Lys  Ala  Arg
 1              5                        10                       15

Arg  Cys  Leu  Gly  Arg  Ser  Lys  Arg  Asn  Thr  Gly  Thr  Lys  Ser  Leu  Gly
          20                       25                       30

Pro  Ile  Cys  Ser
          35
```

( 2 ) INFORMATION FOR SEQ ID NO:8:

( i ) SEQUENCE CHARACTERISTICS:
  ( A ) LENGTH: 4794 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:8:

```
GGTACCGTGA GGCGATGGGT GGCCCGGGGC CCGGCTGTCT GGTAAGCGCG GCCGCAAAAC      60
AGCTGTACTC TCGAATCCCA GTTAGTAACA ATGTGCTATG GAATCTCCAA TGACGAGCAC     120
ACTTCACCGA ACCCCATTAG CCACCGCGGG GCTGGCGCTC GTAGTGGCGC TGGGTGGCTG     180
CGGGGGCGGG GGCGGTGACA GTCGAGAGAC ACCGCCATAC GTGCCGAAAG CGACGACCGT     240
CGACGCAACA ACGCCGGCGC CGGCCGCCGA GCCACTGACG ATCGCCAGTC CCATGTTCGC     300
CGACGGCGCC CCGATCCCGG TGCAATTCAG CTGCAAGGGG CCAACGTGG  CCGCCACCGT     360
TGACGTGGTC GTCGCCCGCG GCGAGCGAAC TGGCACTCGT CGTCGATGAC CCCGACGCGG     420
TCGGCGGACT GTACGTGCAC TGGATCGTGA CCGGAATCGC CCCTGGCTCT GGCAGCACGG     480
CGGATGGTCA GACTCCTGCT GGTGGGCACA GCGTGCCGAA TTCTGGTGGT CGGCAAGGAT     540
ACTTCGGTCC ATGCCCGCCG GCGGGCACCG GACACACCA  CTACCGGTTT ACCCTCTACC     600
ACCTTCCTGT CGCGCTCCAG CTGCCACCGG GAGCCACGGG AGTCCAAGCG GCACAGGCGA     660
TAGCACAGGC CGCCAGCGAC AGGCCCGGCT CGTCGGCACA TTCGAAGGCT GACGCCGCGG     720
CATCCCTGGC GAGGTGGTCG AAACCCTGGC TTCTCCAATT GCGCCTGGCG ACAATGATCA     780
ATATGGAATC GACAGTGGCG CACGCATTTC ACCGGTTCGC ACTGGCCATC TTGGGGCTGG     840
CGCTCCCCGT GGCGCTAGTT GCCTACGGTG GCAACGGTGA CAGTCGAAAG GCGGCGGCCG     900
TGGCGCCGAA AGCAGCAGCG CTCGGTCGGA GTATGCCCGA AACGCCTACC GGCGATGTAC     960
TGACAATCAG CAGTCCGGCA TTCGCCGACG GTGCGCCGAT CCCGGAACAG TACACCTGCA    1020
AAGGAGCCAA TATCGCGGCC TCCGTTGACC TGGTCGGCGC CGTTTGGCGG CGCACTCGTT    1080
GTCGATGATC CGGACCACCT CGCGAACCTT ACGTCCATTG GATCGTGATC GGGATCGCCC    1140
CTGGTGCTGG CAGCAGCCGA TGGTGAGACT CCCGGTGGCG GAATCAGCCT GCCGAACTCC    1200
AGCGGTCAGC CCGCATACAC CGGCCCCTGC CCGCCGGCGG GCACCGGGAC ACACCACTAC    1260
CGGTTTACCC TCTACCACCT TCCTGCCGTG CCTCCACTCG CGGGACTGGC TGGGACACAA    1320
GCGGCGCGGG TGATCGCGCA GGCCGCCACC ATGCAGGCCC GGCTCATCGG AACATACGAA    1380
GGCTGATCCA CCCGCCATCC CACGATCCAG CGGCCCCGGG CGATCGGGTC CTAGCAGACG    1440
CCTGTCACGC TAGCCAAAGT CTTGACTGAT TCCAGAAAAG GGAGTCATAT TGTCTAGTGT    1500
GTCCTCTATA CCGGACTACG CCGAACAGCT CCGGACGGCC GACCTGCGCG TGACCCGACC    1560
```

```
GCGCGTCGCC GTCCTGGAAG CAGTGAATGC GCATCCACAC GCCGACACGG AAACGATTTT    1620
CGGTGCCGTG CGTTTTGCGC TGCCCGACGT ATCCGGCAAG CCGTGTACGA CGTGCTGCAT    1680
GCCCTGACCG CCGCGGGCTT GGTGCGAAAG ATCCAACCCT CGGGCTCCGT CGCGCGCTAC    1740
GAGTCCAGGG TCGGCGACAA CCACCATCAC ATCGTCTGCC GGTCTTGCGG GGTTATCGCC    1800
GATGTCGACT GTGCTGTTGG CGAGGCACCC TGTCTGACGG CCTCGGACCA TAACGGCTTC    1860
CTGTTGGACG AGGCGGAGGT CATCTACTGG GGTCTATGTC CTGATTGTTC GATATCCGAC    1920
ACTTCGCGAT CACATCCGTG ATCACAGCCC GATAACACCA ACTCCTGGAA GGAATGCTGT    1980
GCCCGAGCAA CACCCACCCA TTACAGAAAC CACCACCGGA GCCGCTAGCA ACGGCTGTCC    2040
CGTCGTGGGT CATATGAAAT ACCCCGTCGA GGGCGGCGGA AACCAGGACT GGTGGCCCAA    2100
CCGGCTCAAT CTGAAGGTAC TGCACCAAAA CCCGGCCGTC GCTGACCCGA TGGGTGCGGC    2160
GTTCGACTAT GCCGCGGAGG TCGCGACCAG TCGACTTGAC GCCCTGACGC GGGACATCGA    2220
GGAAGTGATG ACCACCTCGC AGCCGTGGTG GCCCGCCGAC TACGGCCACT ACGGGCCGCT    2280
GTTTATCCGG ATGGCGTGGC ACGCTGCCGG CACCTACCGC ATCCACGACG GCCGCGGCGG    2340
CGCCGGGGGC GGCATGCAGC GGTTCGCGCC GCTTAACAGC TGGCCCGACA ACGCCAGCTT    2400
GGACAAGGCG CGCCGGCTGC TGTGGCCGGT CAAGAAGAAG TACGGCAAGA AGCTCTCATG    2460
GGCGGACCTG ATTGTTTTCG CCGGCAACCG CTGCGCTCGG AATCGATGGG CTTCAAGACG    2520
TTCGGGTTCG GCTTCGGGCG TCGACCAGTG GGAGACCGAT GAGGTCTATT GGGGCAAGGA    2580
AGCCACCTGG CTCGGCGATG ACGGTTACAG CGTAAGCGAT CTGGAGAACC CGCTGGCCGC    2640
GGTGCAGATG GGGCTGATCT ACGTGAACCC GGAGGCGCCG AACGGCAACC CGGACCCCAT    2700
GGCCGCGGCG GTCGACATTC GCGAGACGTT TCGGCGCATG GCCATGAACG ACGTCGAAAC    2760
AGCGGCGCTG ATCGTCGGCG GTCACACTTT CGGTAAGACC CATGGCGCCG GCCCGGCCGA    2820
TCTGGTCGGC CCCGAACCCG AGGCTGCTCC GCTGGAGCAG ATGGGCTTGG GCTGGAAGAG    2880
CTCGTATGGC ACCGGAACCG GTAAGGACGC GATCACCAGC GGCATCGAGG TCGTATGGAC    2940
GAACACCCCG ACGAAATGGG ACAACAGTTT CCTCGAGATC CTGTACGGCT ACGAGTGGGA    3000
GCTGACGAAG AGCCCTGCTG GCGCTTGGCA ATACACCGCC AAGGACGGCG CCGGTGCCGG    3060
CACCATCCCG GACCCGTTCG GCGGGCCAGG GCGCTCCCCG ACGATGCTGG CCACTGACCT    3120
CTCGCTGCGG GTGGATCCGA TCTATGAGCG GATCACGCGT CGCTGGCTGG AACACCCCGA    3180
GGAATTGGCC GACGAGTTCC GCAAGGCCTG GTACAAGCTG ATCCACGAG ACATGGGTCC    3240
CGTTGCGAGA TACCTTGGGC CGCTGGTCCC CAAGCAGACC CTGCTGTGGC AGGATCCGGT    3300
CCCTGCGGTC AGCACGACCT CGTCGGCGAA GCAGATTGCC AGCCTTAAGA GCCAGATCCG    3360
GGCATCGGGA TTGACTGTCT CACAGCTAGT TTCGACCGCA TGGGCGGCGG CGTCGTCGTT    3420
CCGTGGTAGC GACAAGCGCG GCGGCGCCAA CGGTGGTCGC ATCCGCCTGC AGCCACAAGT    3480
CGGGTGGGAG GTCAACGACC CCGACGGATC TGCGCAAGGT CATTCGCACC CTGAAGAGAT    3540
CCAGGAGTCA TTCACTCGGC GCGGGAACAT CAAAGTGTCC TTCGCCGACC TCGTCGTGCT    3600
CGGTGGCTGT GCGCCACTAG AGAAAGCAGC AAAGGCGGCT GGCCACAACA TCACGGTGCC    3660
CTTCACCCCG GGCCCGCACG ATGCGTCGCA GGAACAAACC GACGTGGAAT CCTTTGCCGT    3720
GCTGGAGCCC AAGGCAGATG GCTTCCGAAA CTACCTCGGA AAGGGCAACC GTTGCCGGCC    3780
GAGTACATCG CTGCTCGACA AGGCGAACCT GCTTACGCTC AGTGCCCCTG AGATGACGGT    3840
GCTGGTAGGT GGCCTGCGCG TCCTCGGCGC AAACTACAAG CGCTTACCGC TGGGCGTGTT    3900
CACCGAGGCC TCCGAGTCAC TGACCAACGA CTTCTTCGTG AACCTGCTCG ACATGGGTAT    3960
```

| | | | | | |
|---|---|---|---|---|---|
| CACCTGGGAG | CCCTCGCCAG | CAGATGACGG | GACCTACCAG | GGAAGGATGG | CAGTGGCAAG | 4020 |
| GTGAAGTGGA | CCGGCAGCCG | CGTGGACCTG | GTCTTCGGGT | CCAACTCGGA | GTTGCGGGCG | 4080 |
| CTTGTCGAGG | TCTATGCGCC | GATGACGCGG | CAGGCGAAGT | TCGTGACAGG | ATTCGTCGCT | 4140 |
| GCGTGGGACA | AGGTGATGAA | CCTCGACAGG | TTCGACGTGC | GCTGATTCGG | GTTGATCGGC | 4200 |
| CCTGCCCGCC | GATCAACCAC | AACCCGCCGC | AGCACCCGC | GAGCTGACCG | GCTCGCGGGG | 4260 |
| TGCTGGTGTT | TGCCCGGCGC | GATTTGTCAG | ACCCGCGTG | CATGGTGGTC | GCACGGACGC | 4320 |
| ACGAGACGGG | GATGACGAGA | CGGGGATGAG | GAGAAAGGGC | GCCGAAATGT | GCTGGATGTG | 4380 |
| CGATCACCCG | GAAGCCACCG | CCGAGGAGTA | CCTCGACGAG | GTGTACGGGA | TAATGCTCAT | 4440 |
| GCATGGCTGG | GCGGTACAGC | ACGTGGAGTG | CGAGCGACGG | CCATTTGCCT | ACACGGTTGG | 4500 |
| TCTAACCCGG | CGCGGCTTGC | CCGAACTGGT | GGTGACTGGC | CTCTCGCCAC | GACGTGGGCA | 4560 |
| GCGGTTGTTG | AACATGCCGT | CGAGGGCTCT | GGTCGGTGAC | TTGCTGACTC | CCGGTATGTA | 4620 |
| GACCACCCTC | AAAGCCGGCC | CTCTTGTCGA | AACGGTCCAG | GCTACACATC | CGGACGCGCA | 4680 |
| TTTGTATTGT | GCGATCGCCA | TCTTTGCGCA | CAAGGTGACG | GCCTTGCAGT | TGGTGTGGGC | 4740 |
| CGACCGCGTG | GTCGCTGGCC | GTGGGCGGCG | GACTTCGACG | AAGGTCGCGG | TACC | 4794 |

(2) INFORMATION FOR SEQ ID NO:9:

(i) SEQUENCE CHARACTERISTICS:
(A) LENGTH: 735 amino acids
(B) TYPE: amino acid
(D) TOPOLOGY: linear (ii) MOLECULE TYPE: peptide (xi) SEQUENCE DESCRIPTION: SEQ ID NO:9:

```
Met Pro Glu Gln His Pro Pro Ile Thr Glu Thr Thr Thr Gly Ala Ala
 1               5                  10                  15
Ser Asn Gly Cys Pro Val Val Gly His Met Lys Tyr Pro Val Glu Gly
            20                  25                  30
Gly Gly Asn Gln Asp Trp Trp Pro Asn Arg Leu Asn Leu Lys Val Leu
        35                  40                  45
His Gln Asn Pro Ala Val Ala Asp Pro Met Gly Ala Ala Phe Asp Tyr
    50                  55                  60
Ala Ala Glu Val Ala Thr Ser Arg Leu Asp Ala Leu Thr Arg Asp Ile
65                  70                  75                  80
Glu Glu Val Met Thr Thr Ser Gln Pro Trp Trp Pro Ala Asp Tyr Gly
                85                  90                  95
His Tyr Gly Pro Leu Phe Ile Arg Met Ala Trp His Ala Ala Gly Thr
            100                 105                 110
Tyr Arg Ile His Asp Gly Arg Gly Gly Ala Gly Gly Gly Met Gln Arg
        115                 120                 125
Phe Ala Pro Leu Asn Ser Trp Pro Asp Asn Ala Ser Leu Asp Lys Ala
    130                 135                 140
Arg Arg Leu Leu Trp Pro Val Lys Lys Lys Tyr Gly Lys Lys Leu Ser
145                 150                 155                 160
Trp Ala Asp Leu Ile Val Phe Ala Gly Asn Arg Cys Ala Arg Asn Arg
                165                 170                 175
Trp Ala Ser Arg Arg Ser Gly Ser Ala Ser Gly Val Asp Gln Trp Glu
            180                 185                 190
Thr Asp Glu Val Tyr Trp Gly Lys Glu Ala Thr Trp Leu Gly Asp Asp
        195                 200                 205
```

```
Gly Tyr Ser Val Ser Asp Leu Glu Asn Pro Leu Ala Ala Val Gln Met
    210             215             220
Gly Leu Ile Tyr Val Asn Pro Glu Ala Pro Asn Gly Asn Pro Asp Pro
225             230             235             240
Met Ala Ala Ala Val Asp Ile Arg Glu Thr Phe Arg Arg Met Ala Met
                245             250                     255
Asn Asp Val Glu Thr Ala Ala Leu Ile Val Gly Gly His Thr Phe Gly
            260             265             270
Lys Thr His Gly Ala Gly Pro Ala Asp Leu Val Gly Pro Glu Pro Glu
        275             280             285
Ala Ala Pro Leu Glu Gln Met Gly Leu Gly Trp Lys Ser Ser Tyr Gly
    290             295             300
Thr Gly Thr Gly Lys Asp Ala Ile Thr Ser Gly Ile Glu Val Val Trp
305             310             315                     320
Thr Asn Thr Pro Thr Lys Trp Asp Asn Ser Phe Leu Glu Ile Leu Tyr
                325             330             335
Gly Tyr Glu Trp Glu Leu Thr Lys Ser Pro Ala Gly Ala Trp Gln Tyr
            340             345             350
Thr Ala Lys Asp Gly Ala Gly Ala Gly Thr Ile Pro Asp Pro Phe Gly
        355             360             365
Gly Pro Gly Arg Ser Pro Thr Met Leu Ala Thr Asp Leu Ser Leu Arg
    370             375             380
Val Asp Pro Ile Tyr Glu Arg Ile Thr Arg Arg Trp Leu Glu His Pro
385             390             395                     400
Glu Glu Leu Ala Asp Glu Phe Arg Lys Ala Trp Tyr Lys Leu Ile His
                405             410             415
Arg Asp Met Gly Pro Val Ala Arg Tyr Leu Gly Pro Leu Val Pro Lys
            420             425             430
Gln Thr Leu Leu Trp Gln Asp Pro Val Pro Ala Val Ser Thr Thr Ser
        435             440             445
Ser Ala Lys Gln Ile Ala Ser Leu Lys Ser Gln Ile Arg Ala Ser Gly
    450             455             460
Leu Thr Val Ser Gln Leu Val Ser Thr Ala Trp Ala Ala Ala Ser Ser
465             470             475                     480
Phe Arg Gly Ser Asp Lys Arg Gly Gly Ala Asn Gly Gly Arg Ile Arg
                485             490             495
Leu Gln Pro Gln Val Gly Trp Glu Val Asn Asp Pro Asp Gly Ser Ala
            500             505             510
Gln Gly His Ser His Pro Glu Glu Ile Gln Glu Ser Phe Thr Arg Arg
        515             520             525
Gly Asn Ile Lys Val Ser Phe Ala Asp Leu Val Val Leu Gly Gly Cys
    530             535             540
Ala Pro Leu Glu Lys Ala Ala Lys Ala Ala Gly His Asn Ile Thr Val
545             550             555                     560
Pro Phe Thr Pro Gly Pro His Asp Ala Ser Gln Glu Gln Thr Asp Val
                565             570                     575
Glu Ser Phe Ala Val Leu Glu Pro Lys Ala Asp Gly Phe Arg Asn Tyr
            580             585             590
Leu Gly Lys Gly Asn Arg Cys Arg Pro Ser Thr Ser Leu Leu Asp Lys
        595             600             605
Ala Asn Leu Leu Thr Leu Ser Ala Pro Glu Met Thr Val Leu Val Gly
    610             615             620
Gly Leu Arg Val Leu Gly Ala Asn Tyr Lys Arg Leu Pro Leu Gly Val
625             630             635                     640
```

|     |     |     |     |     |     |     |     |     |     |     |     |     |     |     |
|-----|-----|-----|-----|-----|-----|-----|-----|-----|-----|-----|-----|-----|-----|-----|
| Phe | Thr | Glu | Ala | Ser | Glu | Ser | Leu | Thr | Asn | Asp | Phe | Phe | Val | Asn | Leu |
|     |     |     |     | 645 |     |     |     |     | 650 |     |     |     |     | 655 |
| Leu | Asp | Met | Gly | Ile | Thr | Trp | Glu | Pro | Ser | Pro | Ala | Asp | Asp | Gly | Thr |
|     |     |     | 660 |     |     |     |     | 665 |     |     |     |     | 670 |     |
| Tyr | Gln | Gly | Lys | Asp | Gly | Ser | Gly | Lys | Val | Lys | Trp | Thr | Gly | Ser | Arg |
|     |     | 675 |     |     |     |     | 680 |     |     |     |     | 685 |     |     |
| Val | Asp | Leu | Val | Phe | Gly | Ser | Asn | Ser | Glu | Leu | Arg | Ala | Leu | Val | Glu |
|     | 690 |     |     |     |     | 695 |     |     |     |     | 700 |     |     |     |
| Val | Tyr | Ala | Pro | Met | Thr | Arg | Gln | Ala | Lys | Phe | Val | Thr | Gly | Phe | Val |
| 705 |     |     |     |     | 710 |     |     |     |     | 715 |     |     |     |     | 720 |
| Ala | Ala | Trp | Asp | Lys | Val | Met | Asn | Leu | Asp | Arg | Phe | Asp | Val | Arg |
|     |     |     |     | 725 |     |     |     |     | 730 |     |     |     |     | 735 |

( 2 ) INFORMATION FOR SEQ ID NO:10:

( i ) SEQUENCE CHARACTERISTICS:
        ( A ) LENGTH: 699 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

| | | | | | |
|---|---|---|---|---|---|
| TTCGAAGGCT | GACGCCGCGG | CATCCCTGGC | GAGGTGGTCG | AAACCCTGGC | TTCTCCAATT | 60 |
| GCGCCTGGCG | ACAATGATCA | ATATGGAATC | GACAGTGGCG | CACGCATTTC | ACCGGTTCGC | 120 |
| ACTGGCCATC | TTGGGGCTGG | CGCTCCCCGT | GGCGCTAGTT | GCCTACGGTG | GCAACGGTGA | 180 |
| CAGTCGAAAG | GCGGCGGCCG | TGGCGCCGAA | AGCAGCAGCG | CTCGGTCCGA | GTATGCCCGA | 240 |
| AACGCCTACC | GGCGATGTAC | TGACAATCAG | CAGTCCGGCA | TTCGCCGACG | GTGCGCCGAT | 300 |
| CCCGGAACAG | TACACCTGCA | AAGGAGCCAA | TATCGCGGCC | TCCGTTGACG | TGGTCGGCGC | 360 |
| CGTTTGGCGG | CGCACTCGTT | GTCGATGATC | CGGACCACCT | CGCGAACTTA | CGTCCATTGG | 420 |
| ATCGTGATCG | GGATCGCCCC | TGGTGCTGGC | AGCAGCCGAT | GGTGAGACTC | CCGGTGGCGG | 480 |
| AATCAGCCTG | CCGAACTCCA | GCGGTCAGCC | CGCATACACC | GGCCCCTGCC | CGCCGGCGGG | 540 |
| CACCGGGACA | CACCACTACC | GGTTTACCCT | CTACCACCTT | CCTGCCGTGC | CTCCACTCGC | 600 |
| GGGACTGGCT | GGGACACAAG | CGGCGCGGGT | GATCGCGCAG | GCCGCCACCA | TGCAGGCCCG | 660 |
| GCTCATCGGA | ACATACGAAG | CTGATCCAC | CCGCCATCC | | | 699 |

( 2 ) INFORMATION FOR SEQ ID NO:11:

( i ) SEQUENCE CHARACTERISTICS:
        ( A ) LENGTH: 700 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| GGTACCGTGA | GGCGATGGGT | GGCCCGGGGC | CGGCTGTCT | GGTAAGCGCG | GCCGCAAAAC | 60 |
| AGCTGTACTC | TCGAATCCCA | GTTAGTAACA | ATGTGCTATG | GAATCTCCAA | TGACGAGCAC | 120 |
| ACTTCACCGA | ACCCCATTAG | CCACCGCGGG | GCTGGCGCTC | GTAGTGGCGC | TGGGTGGCTG | 180 |
| CGGGGGCGGG | GGCGGTGACA | GTCGAGAGAC | ACCGCCATAC | GTGCCGAAAG | CGACGACCGT | 240 |
| CGACGCAACA | ACGCCGGCGC | CGGCCGCCGA | GCCACTGACG | ATCGCCAGTC | CCATGTTCGC | 300 |
| CGACGGCGCC | CCGATCCCGG | TGCAATTCAG | CTGCAAGGGG | GCCAACGTGG | CCGCCACCGT | 360 |

-continued

```
TGACGTGGTC  GTCGCCCGCG  GCGAGCGAAC  TGGCACTCGT  CGTCGATGAC  CCCGACGCGG    420

TCGGCGGACT  GTACGTGCAC  TGGATCGTGA  CCGGAATCGC  CCCTGGCTCT  GGCAGCACGG    480

CGGATGGTCA  GACTCCTGCT  GGTGGGCACA  GCGTGCCGAA  TTCTGGTGGT  CGGCAAGGAT    540

ACTTCGGTCC  ATGCCCGCCG  GCGGGCACCG  GGACACACCA  CTACCGGTTT  ACCCTCTACC    600

ACCTTCCTGT  CGCGCTCCAG  CTGCCACCGG  GAGCCACGGG  AGTCCAAGCG  GCACAGGCGA    660

TAGCACAGGC  CGCCAGCGAC  AGGCCCGGCT  CGTCGGCACA                            700
```

( 2 ) INFORMATION FOR SEQ ID NO:12:

( i ) SEQUENCE CHARACTERISTICS:
        ( A ) LENGTH: 735 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Met  Pro  Glu  Gln  His  Pro  Pro  Ile  Thr  Glu  Thr  Thr  Thr  Gly  Ala  Ala
  1              5                   10                       15

Ser  Asn  Gly  Cys  Pro  Val  Val  Gly  His  Met  Lys  Tyr  Pro  Val  Glu  Gly
              20                   25                       30

Gly  Gly  Asn  Gln  Asp  Trp  Trp  Pro  Asn  Arg  Leu  Asn  Leu  Lys  Val  Leu
          35                   40                       45

His  Gln  Asn  Pro  Ala  Val  Ala  Asp  Pro  Met  Gly  Ala  Ala  Phe  Asp  Tyr
      50                   55                       60

Ala  Ala  Glu  Val  Ala  Thr  Ser  Leu  Arg  Asp  Ala  Leu  Thr  Arg  Asp  Ile
 65                   70                       75                        80

Glu  Glu  Val  Met  Thr  Thr  Ser  Gln  Pro  Trp  Trp  Pro  Ala  Asp  Tyr  Gly
                85                       90                       95

His  Tyr  Gly  Pro  Leu  Phe  Ile  Arg  Met  Ala  Trp  His  Ala  Ala  Gly  Thr
               100                      105                      110

Tyr  Arg  Ile  His  Asp  Gly  Arg  Gly  Gly  Ala  Gly  Gly  Gly  Met  Gln  Arg
          115                      120                      125

Phe  Ala  Pro  Leu  Asn  Ser  Trp  Pro  Asp  Asn  Ala  Ser  Leu  Asp  Lys  Ala
     130                      135                      140

Arg  Arg  Leu  Leu  Trp  Pro  Val  Lys  Lys  Lys  Tyr  Gly  Lys  Lys  Leu  Ser
145                      150                      155                     160

Trp  Ala  Asp  Leu  Ile  Val  Phe  Ala  Gly  Asn  Arg  Cys  Ala  Arg  Asn  Arg
               165                      170                      175

Trp  Ala  Ser  Arg  Arg  Ser  Gly  Ser  Ala  Ser  Gly  Val  Asp  Gln  Trp  Glu
               180                      185                      190

Thr  Asp  Glu  Val  Tyr  Trp  Gly  Lys  Glu  Ala  Thr  Trp  Leu  Gly  Asp  Asp
          195                      200                      205

Gly  Tyr  Ser  Val  Ser  Asp  Leu  Glu  Asn  Pro  Leu  Ala  Ala  Val  Gln  Met
     210                      215                      220

Gly  Leu  Ile  Tyr  Val  Asn  Pro  Glu  Ala  Pro  Asn  Gly  Asn  Pro  Asp  Pro
225                      230                      235                     240

Met  Ala  Ala  Ala  Val  Asp  Ile  Arg  Glu  Thr  Phe  Arg  Arg  Met  Ala  Met
               245                      250                      255

Asn  Asp  Val  Glu  Thr  Ala  Ala  Leu  Ile  Val  Gly  Gly  His  Thr  Phe  Gly
               260                      265                      270

Lys  Thr  His  Gly  Ala  Gly  Pro  Ala  Asp  Leu  Val  Gly  Pro  Glu  Pro  Glu
          275                      280                      285

Ala  Ala  Pro  Leu  Glu  Gln  Met  Gly  Leu  Gly  Trp  Lys  Ser  Ser  Tyr  Gly
```

|     |     |     |     |     | 290 |     |     |     |     | 295 |     |     |     |     | 300 |     |     |     |     |
|-----|-----|-----|-----|-----|-----|-----|-----|-----|-----|-----|-----|-----|-----|-----|-----|-----|-----|-----|-----|
| Thr 305 | Gly | Thr | Gly | Lys | Asp 310 | Ala | Ile | Thr | Ser | Gly 315 | Ile | Glu | Val | Val | Trp 320 |
| Thr | Asn | Thr | Pro | Thr 325 | Lys | Trp | Asp | Asn | Ser 330 | Phe | Leu | Glu | Ile | Leu 335 | Tyr |
| Gly | Tyr | Glu | Trp 340 | Glu | Leu | Thr | Lys | Ser 345 | Pro | Ala | Gly | Ala | Trp 350 | Gln | Tyr |
| Thr | Ala | Lys 355 | Asp | Gly | Ala | Gly 360 | Ala | Gly | Thr | Ile | Pro 365 | Asp | Pro | Phe | Gly |
| Gly | Pro 370 | Gly | Arg | Ser | Pro | Thr 375 | Met | Leu | Ala | Thr | Asp 380 | Leu | Ser | Leu | Arg |
| Val 385 | Asp | Pro | Ile | Tyr | Glu 390 | Arg | Ile | Thr | Arg | Arg 395 | Trp | Leu | Glu | His | Pro 400 |
| Glu | Glu | Leu | Ala | Asp 405 | Glu | Phe | Arg | Lys | Ala 410 | Trp | Tyr | Lys | Leu | Ile 415 | His |
| Arg | Asp | Met | Gly 420 | Pro | Val | Ala | Arg | Tyr 425 | Leu | Gly | Pro | Leu | Val 430 | Pro | Lys |
| Gln | Thr | Leu 435 | Leu | Trp | Gln | Asp | Pro 440 | Val | Pro | Ala | Val | Ser 445 | Thr | Thr | Ser |
| Ser | Ala 450 | Lys | Gln | Ile | Ala | Ser 455 | Leu | Lys | Ser | Gln | Ile 460 | Arg | Ala | Ser | Gly |
| Leu 465 | Thr | Val | Ser | Gln | Leu 470 | Val | Ser | Thr | Ala | Trp 475 | Ala | Ala | Ala | Ser | Ser 480 |
| Phe | Arg | Gly | Ser | Asp 485 | Lys | Arg | Gly | Gly | Ala 490 | Asn | Gly | Gly | Arg | Ile 495 | Arg |
| Leu | Gln | Pro | Gln | Val 500 | Gly | Trp | Glu | Val 505 | Asn | Asp | Pro | Asp | Gly 510 | Ser | Ala |
| Gln | Gly | His | Ser 515 | His | Pro | Glu | Glu 520 | Ile | Gln | Glu | Ser | Phe 525 | Thr | Arg | Arg |
| Gly | Asn | Ile 530 | Lys | Val | Ser | Phe 535 | Ala | Asp | Leu | Val | Val 540 | Leu | Gly | Gly | Cys |
| Ala 545 | Pro | Leu | Glu | Lys | Ala 550 | Ala | Lys | Ala | Ala | Gly 555 | His | Asn | Ile | Thr | Val 560 |
| Pro | Phe | Thr | Pro | Gly 565 | Pro | His | Asp | Ala | Ser 570 | Gln | Glu | Gln | Thr | Asp 575 | Val |
| Glu | Ser | Phe | Ala 580 | Val | Leu | Glu | Pro | Lys 585 | Ala | Asp | Gly | Phe | Arg 590 | Asn | Tyr |
| Leu | Gly | Lys 595 | Gly | Asn | Arg | Cys | Arg 600 | Pro | Ser | Thr | Ser | Leu 605 | Leu | Asp | Lys |
| Ala | Asn 610 | Leu | Leu | Thr | Leu | Ser 615 | Ala | Pro | Glu | Met | Thr 620 | Val | Leu | Val | Gly |
| Gly 625 | Leu | Arg | Val | Leu | Gly 630 | Ala | Asn | Tyr | Lys | Arg 635 | Leu | Pro | Leu | Gly | Val 640 |
| Phe | Thr | Glu | Ala | Ser 645 | Glu | Ser | Leu | Thr | Asn 650 | Asp | Phe | Phe | Val | Asn 655 | Leu |
| Leu | Asp | Met | Gly 660 | Ile | Thr | Trp | Glu | Pro 665 | Ser | Pro | Ala | Asp | Asp 670 | Gly | Thr |
| Tyr | Gln | Gly 675 | Lys | Asp | Gly | Ser | Gly 680 | Lys | Val | Lys | Trp | Thr 685 | Gly | Ser | Arg |
| Val | Asp 690 | Leu | Val | Phe | Gly | Ser 695 | Asn | Ser | Glu | Leu | Arg 700 | Ala | Leu | Val | Glu |
| Val 705 | Tyr | Ala | Pro | Met | Thr 710 | Arg | Gln | Ala | Lys | Phe 715 | Val | Thr | Gly | Phe | Val 720 |

|     |     |     |     |     |     |     |     |     |     |     |     |     |
|-----|-----|-----|-----|-----|-----|-----|-----|-----|-----|-----|-----|-----|
| Ala | Ala | Trp | Asp | Lys | Val | Met | Asn | Leu | Asp | Arg | Phe | Asp | Val | Arg |
|     |     |     |     | 725 |     |     |     | 730 |     |     |     |     |     | 735 |

(2) INFORMATION FOR SEQ ID NO:13:

(i) SEQUENCE CHARACTERISTICS:
        (A) LENGTH: 726 amino acids
        (B) TYPE: amino acid
        (D) TOPOLOGY: linear (ii) MOLECULE TYPE: peptide (xi) SEQUENCE DESCRIPTION: SEQ ID NO:13:

```
Met Ser Thr Ser Asp Ile His Asn Thr Thr Ala Thr Gly Lys Cys
 1               5                  10                  15
Pro Phe His Gln Gly Gly His Asp Gln Ser Ala Gly Ala Gly Thr Thr
            20                  25                  30
Thr Arg Asp Trp Trp Pro Asn Gln Leu Arg Val Asp Leu Leu Asn Gln
            35                  40                  45
His Ser Asn Arg Ser Asn Pro Leu Gly Glu Asp Phe Asp Tyr Arg Lys
 50                  55                  60
Glu Phe Ser Lys Leu Asp Tyr Tyr Gly Leu Lys Lys Asp Leu Lys Ala
 65                  70                  75                  80
Leu Leu Thr Glu Ser Gln Pro Trp Trp Pro Ala Asp Trp Gly Ser Tyr
                 85                  90                  95
Ala Gly Leu Phe Ile Arg Met Ala Trp His Gly Ala Gly Thr Tyr Arg
                100                 105                 110
Ser Ile Asp Gly Arg Gly Gly Ala Gly Arg Gly Gln Gln Arg Phe Ala
                115                 120                 125
Pro Leu Asn Ser Trp Pro Asp Asn Val Ser Leu Asp Lys Ala Arg Arg
            130                 135                 140
Leu Leu Trp Pro Ile Lys Gln Lys Tyr Gly Gln Lys Ile Ser Trp Ala
145                 150                 155                 160
Asp Leu Phe Ile Leu Ala Gly Asn Val Ala Leu Glu Asn Ser Gly Phe
                165                 170                 175
Arg Thr Phe Gly Phe Gly Ala Gly Arg Glu Asp Val Trp Glu Pro Asp
                180                 185                 190
Leu Asp Val Asn Trp Gly Asp Glu Lys Ala Trp Leu Thr His Arg His
            195                 200                 205
Pro Glu Ala Leu Ala Lys Ala Pro Leu Gly Ala Thr Glu Met Gly Leu
            210                 215                 220
Ile Tyr Val Asn Pro Glu Gly Pro Asp His Ser Gly Glu Pro Leu Ser
225                 230                 235                 240
Ala Ala Ala Ala Ile Arg Ala Thr Phe Gly Asn Met Gly Met Asn Asp
                245                 250                 255
Glu Glu Thr Val Ala Leu Ile Ala Gly Gly His Thr Leu Gly Lys Thr
            260                 265                 270
His Gly Ala Gly Pro Thr Ser Asn Val Gly Pro Asp Pro Glu Ala Ala
            275                 280                 285
Pro Ile Glu Glu Gln Gly Leu Gly Trp Ala Ser Thr Tyr Gly Ser Gly
     290                 295                 300
Val Gly Ala Asp Ala Ile Thr Ser Gly Leu Glu Val Val Trp Thr Gln
305                 310                 315                 320
Thr Pro Thr Gln Trp Ser Asn Tyr Phe Phe Glu Asn Leu Phe Lys Tyr
                325                 330                 335
Glu Trp Val Gln Thr Arg Ser Pro Ala Gly Ala Ile Gln Phe Glu Ala
            340                 345                 350
```

Val Asp Ala Pro Glu Ile Ile Pro Asp Pro Phe Asp Pro Ser Lys Lys
            355                 360                 365
Arg Lys Pro Thr Met Leu Val Thr Asp Leu Thr Leu Arg Phe Asp Pro
        370                 375                 380
Glu Phe Glu Lys Ile Ser Arg Arg Phe Leu Asn Asp Pro Gln Ala Phe
385                 390                 395                 400
Asn Glu Ala Phe Ala Arg Ala Trp Phe Lys Leu Thr His Arg Asp Met
                405                 410                 415
Gly Pro Lys Ser Arg Tyr Ile Gly Pro Glu Val Pro Lys Glu Asp Leu
            420                 425                 430
Ile Trp Gln Asp Pro Leu Pro Gln Pro Ile Tyr Asn Pro Thr Glu Gln
            435                 440                 445
Asp Ile Ile Asp Leu Lys Phe Ala Ile Ala Asp Ser Gly Leu Ser Val
        450                 455                 460
Ser Glu Leu Val Ser Val Ala Trp Ala Ser Ala Ser Thr Phe Arg Gly
465                 470                 475                 480
Gly Asp Lys Arg Gly Gly Ala Asn Gly Ala Arg Leu Ala Leu Met Pro
                485                 490                 495
Gln Arg Asp Trp Asp Val Asn Ala Ala Ala Val Arg Ala Leu Pro Val
            500                 505                 510
Leu Glu Lys Ile Gln Lys Glu Ser Gly Lys Ala Ser Leu Ala Asp Ile
        515                 520                 525
Ile Val Leu Ala Gly Val Val Gly Val Glu Lys Ala Ala Ser Ala Ala
    530                 535                 540
Gly Leu Ser Ile His Val Pro Phe Ala Pro Gly Arg Val Asp Ala Arg
545                 550                 555                 560
Gln Asp Gln Thr Asp Ile Glu Met Phe Glu Leu Leu Glu Pro Ile Ala
            565                 570                 575
Asp Gly Phe Arg Asn Tyr Arg Ala Arg Leu Asp Val Ser Thr Thr Glu
            580                 585                 590
Ser Leu Leu Ile Asp Lys Ala Gln Gln Leu Thr Leu Thr Ala Pro Glu
        595                 600                 605
Met Thr Ala Leu Val Gly Gly Met Arg Val Leu Gly Gly Asn Phe Asp
    610                 615                 620
Gly Ser Lys Asn Gly Val Phe Thr Asp Arg Val Gly Val Leu Ser Asn
625                 630                 635                 640
Asp Phe Phe Val Asn Leu Leu Asp Met Arg Tyr Glu Trp Lys Ala Thr
                645                 650                 655
Asp Glu Ser Lys Glu Leu Phe Glu Gly Arg Asp Arg Glu Thr Gly Glu
            660                 665                 670
Val Lys Phe Thr Ala Ser Arg Ala Asp Leu Val Phe Gly Ser Asn Ser
        675                 680                 685
Val Leu Arg Ala Val Ala Glu Val Tyr Ala Ser Ser Asp Ala His Glu
    690                 695                 700
Lys Phe Val Lys Asp Phe Val Ala Ala Trp Val Lys Val Met Asn Leu
705                 710                 715                 720
Asp Arg Phe Asp Leu Leu
            725

( 2 ) INFORMATION FOR SEQ ID NO:14:

( i ) SEQUENCE CHARACTERISTICS:
( A ) LENGTH: 729 amino acids
( B ) TYPE: amino acid
( D ) TOPOLOGY: linear ( i i ) MOLECULE TYPE: peptide ( x i ) SEQUENCE DESCRIPTION: SEQ ID NO:14:

| Met | Ser | Thr | Thr | Asp | Asp | Thr | His | Asn | Thr | Leu | Ser | Thr | Gly | Lys | Cys |
|---|---|---|---|---|---|---|---|---|---|---|---|---|---|---|---|
| 1 | | | | 5 | | | | | 10 | | | | | 15 | |
| Pro | Phe | His | Gln | Gly | Gly | His | Asp | Arg | Ser | Ala | Gly | Ala | Gly | Thr | Ala |
| | | | 20 | | | | 25 | | | | | 30 | | | |
| Ser | Arg | Asp | Trp | Trp | Pro | Asn | Gln | Leu | Arg | Val | Asp | Leu | Leu | Asn | Gln |
| | | 35 | | | | 40 | | | | | 45 | | | | |
| His | Ser | Asn | Arg | Ser | Asn | Pro | Leu | Gly | Glu | Asp | Phe | Asp | Tyr | Arg | Lys |
| | 50 | | | | | 55 | | | | | 60 | | | | |
| Glu | Phe | Ser | Lys | Leu | Asp | Tyr | Tyr | Ser | Ala | Leu | Lys | Gly | Asp | Leu | Lys |
| 65 | | | | | 70 | | | | | 75 | | | | | 80 |
| Ala | Leu | Leu | Thr | Asp | Ser | Gln | Pro | Trp | Trp | Pro | Ala | Asp | Trp | Gly | Ser |
| | | | | 85 | | | | | 90 | | | | | 95 | |
| Tyr | Val | Gly | Leu | Phe | Ile | Arg | Met | Ala | Trp | His | Gly | Ala | Gly | Thr | Tyr |
| | | | 100 | | | | | 105 | | | | | 110 | | |
| Arg | Ser | Ile | Asp | Gly | Arg | Gly | Gly | Ala | Gly | Arg | Gly | Gln | Gln | Arg | Phe |
| | | 115 | | | | | 120 | | | | | 125 | | | |
| Ala | Pro | Leu | Asn | Ser | Trp | Pro | Asp | Thr | Val | Ser | Leu | Asp | Lys | Ala | Arg |
| | 130 | | | | | 135 | | | | | 140 | | | | |
| Arg | Leu | Leu | Trp | Pro | Ile | Lys | Gln | Lys | Tyr | Gly | Gln | Lys | Ile | Ser | Trp |
| 145 | | | | | 150 | | | | | 155 | | | | | 160 |
| Ala | Asp | Leu | Phe | Ile | Leu | Ala | Gly | Asn | Val | Ala | Leu | Glu | Asn | Ser | Gly |
| | | | | 165 | | | | | 170 | | | | | 175 | |
| Phe | Arg | Thr | Phe | Gly | Phe | Gly | Ala | Gly | Arg | Glu | Asp | Val | Trp | Glu | Pro |
| | | | 180 | | | | | 185 | | | | | 190 | | |
| Asp | Leu | Asp | Val | Asn | Trp | Gly | Asp | Glu | Lys | Ala | Trp | Leu | Thr | His | Arg |
| | | 195 | | | | | 200 | | | | | 205 | | | |
| His | Pro | Glu | Ala | Leu | Ala | Lys | Ala | Pro | Leu | Gly | Ala | Thr | Glu | Met | Asp |
| | 210 | | | | | 215 | | | | | 220 | | | | |
| Leu | Ile | Tyr | Val | Thr | Pro | Glu | Gly | Pro | Asn | His | Ser | Gly | Glu | Pro | Leu |
| 225 | | | | | 230 | | | | | 235 | | | | | 240 |
| Ser | Ala | Ala | Ala | Ala | Ile | Arg | Ala | Thr | Phe | Gly | Asn | Met | Gly | Met | Asn |
| | | | | 245 | | | | | 250 | | | | | 255 | |
| Asp | Glu | Glu | Thr | Val | Ala | Leu | Ile | Ala | Gly | Gly | His | Thr | Leu | Gly | Lys |
| | | | 260 | | | | | 265 | | | | | 270 | | |
| Thr | His | Gly | Pro | Ala | Ala | Ala | Ser | His | Val | Gly | Ala | Asp | Pro | Glu | Ala |
| | | 275 | | | | | 280 | | | | | 285 | | | |
| Ala | Pro | Ile | Glu | Ala | Gln | Gly | Leu | Gly | Trp | Ala | Ser | Ser | Tyr | Gly | Ser |
| | 290 | | | | | 295 | | | | | 300 | | | | |
| Gly | Val | Gly | Ala | Asp | Ala | Ile | Thr | Ser | Gly | Leu | Glu | Val | Val | Trp | Thr |
| 305 | | | | | 310 | | | | | 315 | | | | | 320 |
| Gln | Thr | Pro | Thr | Gln | Trp | Ser | Asn | Tyr | Phe | Phe | Glu | Asn | Leu | Phe | Lys |
| | | | | 325 | | | | | 330 | | | | | 335 | |
| Tyr | Glu | Trp | Val | Gln | Thr | Arg | Ser | Pro | Ala | Gly | Ala | Ile | Gln | Phe | Glu |
| | | | 340 | | | | | 345 | | | | | 350 | | |
| Ala | Val | Asp | Ala | Pro | Asp | Ile | Ile | Pro | Asp | Pro | Phe | Asp | Pro | Ser | Lys |
| | | 355 | | | | | 360 | | | | | 365 | | | |
| Lys | Arg | Xaa | Xaa | Lys | Pro | Thr | Met | Leu | Val | Thr | Asp | Leu | Thr | Leu | Arg |
| | 370 | | | | | 375 | | | | | 380 | | | | |
| Phe | Asp | Pro | Glu | Phe | Glu | Lys | Ile | Ser | Arg | Arg | Phe | Leu | Asn | Asp | Pro |
| 385 | | | | | 390 | | | | | 395 | | | | | 400 |

```
Gln Ala Phe Asn Glu Ala Phe Ala Arg Ala Trp Phe Lys Leu Thr His
                405                 410                 415
Arg Asp Met Gly Pro Lys Ala Arg Tyr Ile Gly Pro Glu Val Pro Lys
            420                 425                 430
Glu Asp Leu Ile Trp Gln Asp Pro Leu Pro Gln Pro Leu Tyr Gln Pro
        435                 440                 445
Thr Gln Glu Asp Ile Ile Asn Leu Lys Ala Ala Ile Ala Ala Ser Gly
    450                 455                 460
Leu Ser Ile Ser Glu Met Val Ser Val Ala Trp Ala Ser Ala Ser Thr
465                 470                 475                 480
Phe Arg Gly Gly Asp Lys Arg Gly Gly Ala Asn Gly Ala Arg Leu Ala
                485                 490                 495
Leu Ala Pro Gln Arg Asp Trp Asp Val Asn Ala Val Ala Ala Arg Val
            500                 505                 510
Leu Pro Val Leu Glu Glu Ile Gln Lys Thr Thr Asn Lys Ala Ser Leu
        515                 520                 525
Ala Asp Ile Ile Val Leu Ala Gly Val Val Gly Ile Glu Gln Ala Ala
    530                 535                 540
Ala Ala Ala Arg Val Ser Ile His Val Pro Phe Pro Pro Gly Arg Val
545                 550                 555                 560
Asp Ala Arg His Asp Gln Thr Asp Ile Glu Met Phe Ser Leu Leu Glu
                565                 570                 575
Pro Ile Ala Asp Gly Phe Arg Asn Tyr Arg Ala Arg Leu Asp Val Ser
            580                 585                 590
Thr Thr Glu Ser Leu Leu Ile Asp Lys Ala Gln Gln Leu Thr Leu Thr
        595                 600                 605
Ala Pro Glu Met Thr Val Leu Val Gly Gly Met Arg Val Leu Gly Thr
    610                 615                 620
Asn Phe Asp Gly Ser Gln Asn Gly Val Phe Thr Asp Lys Pro Gly Val
625                 630                 635                 640
Leu Ser Thr Asp Phe Phe Ala Asn Leu Leu Asp Met Arg Tyr Glu Trp
                645                 650                 655
Lys Pro Thr Asp Asp Ala Asn Glu Leu Phe Glu Gly Arg Asp Arg Leu
            660                 665                 670
Thr Gly Glu Val Lys Tyr Thr Ala Thr Arg Ala Asp Leu Val Phe Gly
        675                 680                 685
Ser Asn Ser Val Leu Arg Ala Leu Ala Glu Val Tyr Ala Cys Ser Asp
    690                 695                 700
Ala His Glu Lys Phe Val Lys Asp Phe Val Ala Ala Trp Val Lys Val
705                 710                 715                 720
Met Asn Leu Asp Arg Phe Asp Leu Gln
                725
```

( 2 ) INFORMATION FOR SEQ ID NO:15:

( i ) SEQUENCE CHARACTERISTICS:
        ( A ) LENGTH: 731 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Met Glu Asn Gln Asn Arg Gln Asn Ala Ala Gln Cys Pro Phe His Glu
1               5                   10                  15
Ser Val Thr Asn Gln Ser Ser Asn Arg Thr Thr Asn Lys Asp Trp Trp
            20                  25                  30
```

```
Pro  Asn  Gln  Leu  Asn  Leu  Ser  Ile  Leu  His  Gln  His  Asp  Arg  Lys  Thr
          35                       40                 45

Asn  Pro  His  Asp  Glu  Glu  Phe  Asn  Tyr  Ala  Glu  Glu  Phe  Gln  Lys  Leu
     50                       55                 60

Asp  Tyr  Trp  Ala  Leu  Lys  Glu  Asp  Leu  Arg  Lys  Leu  Met  Thr  Glu  Ser
65                       70                 75                            80

Gln  Asp  Trp  Trp  Pro  Ala  Asp  Tyr  Gly  His  Tyr  Gly  Pro  Leu  Phe  Ile
               85                       90                            95

Arg  Met  Ala  Trp  His  Ser  Ala  Gly  Thr  Tyr  Arg  Ile  Gly  Asp  Gly  Arg
               100                      105                      110

Gly  Gly  Ala  Ser  Thr  Gly  Thr  Gln  Arg  Phe  Ala  Pro  Leu  Asn  Ser  Trp
               115                      120                      125

Pro  Asp  Asn  Ala  Asn  Leu  Asp  Lys  Ala  Arg  Arg  Cys  Tyr  Gly  Arg  Ser
     130                      135                      140

Lys  Arg  Asn  Thr  Gly  Thr  Lys  Ser  Leu  Gly  Pro  Ile  Cys  Ser  Phe  Trp
145                           150                      155                      160

Arg  Ala  Met  Ser  Leu  Leu  Asn  Arg  Trp  Val  Glu  Lys  Arg  Leu  Asp  Ser
               165                      170                      175

Ala  Ala  Gly  Pro  Leu  Thr  Ser  Gly  Ile  Arg  Lys  Lys  Thr  Phe  Ile  Gly
               180                      185                      190

Asp  Arg  Lys  Lys  Ser  Gly  Ser  Pro  Leu  Asn  Ala  Ile  Pro  Val  Ile  Ala
          195                      200                      205

Ser  Ser  Lys  Thr  Arg  Ser  Pro  Arg  Ala  Asn  Gly  Val  Asn  Leu  Arg  Gln
     210                      215                      220

Pro  Arg  Arg  Ala  Gly  Arg  Gln  Ala  Gly  Ser  Lys  Ser  Arg  Gly  Ile  Ser
225                           230                      235                      240

Ala  Glu  Thr  Phe  Arg  Arg  Met  Gly  Met  Asn  Asp  Glu  Glu  Thr  Val  Ala
               245                      250                      255

Leu  Ile  Ala  Gly  Gly  His  Thr  Phe  Gly  Lys  Ala  His  Arg  Gly  Gly  Pro
               260                      265                      270

Ala  Thr  His  Val  Gly  Pro  Glu  Pro  Glu  Ala  Ala  Pro  Ile  Glu  Ala  Gln
          275                      280                      285

Gly  Leu  Gly  Trp  Ile  Ser  Ser  Tyr  Gly  Lys  Gly  Lys  Gly  Ser  Asp  Thr
     290                      295                      300

Ile  Thr  Ser  Gly  Ile  Glu  Gly  Ala  Trp  Thr  Thr  Pro  Thr  Pro  Gln  Trp
305                           310                      315                      320

Asp  Thr  Ser  Tyr  Phe  Asp  Met  Leu  Phe  Gly  Tyr  Asp  Trp  Trp  Leu  Thr
                    325                      330                      335

Lys  Ser  Pro  Ala  Gly  Ala  Trp  Gln  Trp  Met  Ala  Val  Asp  Pro  Asp  Glu
               340                      345                      350

Lys  Asp  Leu  Ala  Pro  Asp  Ala  Glu  Asp  Pro  Ser  Lys  Lys  Val  Pro  Thr
          355                      360                      365

Met  Met  Met  Thr  Thr  Asp  Leu  Ala  Leu  Arg  Phe  Asp  Pro  Glu  Tyr  Glu
          370                      375                      380

Lys  Ile  Ala  Arg  Arg  Phe  His  Gln  Asn  Pro  Glu  Glu  Phe  Ala  Glu  Ala
385                      390                      395                           400

Phe  Ala  Arg  Ala  Trp  Phe  Lys  Leu  Thr  His  Arg  Asp  Met  Gly  Pro  Lys
                    405                      410                      415

Thr  Arg  Tyr  Leu  Gly  Pro  Glu  Val  Pro  Lys  Glu  Asp  Phe  Ile  Trp  Gln
               420                      425                      430

Asp  Pro  Ile  Pro  Glu  Val  Asp  Tyr  Glu  Leu  Thr  Glu  Ala  Glu  Ile  Glu
          435                      440                      445

Glu  Ile  Lys  Ala  Lys  Ile  Leu  Asn  Ser  Gly  Leu  Thr  Val  Ser  Glu  Leu
```

|     |     |     |     |     | 450 |     |     |     |     | 455 |     |     |     |     | 460 |     |     |
|-----|-----|-----|-----|-----|-----|-----|-----|-----|-----|-----|-----|-----|-----|-----|-----|-----|-----|
| Val | Lys | Thr | Ala | Trp | Ala | Ser | Ala | Ala | Arg | Ser | Ala | Thr | Arg | Ile | Ser |
| 465 |     |     |     |     | 470 |     |     |     |     | 475 |     |     |     |     | 480 |
| Ala | Ala | Thr | Asn | Gly | Arg | Arg | Ile | Arg | Leu | Ala | Pro | Gln | Lys | Asp | Trp |
|     |     |     |     | 485 |     |     |     |     | 490 |     |     |     |     | 495 |     |
| Glu | Val | Asn | Glu | Pro | Glu | Arg | Leu | Ala | Lys | Val | Leu | Ser | Val | Leu | Arg |
|     |     |     | 500 |     |     |     |     | 505 |     |     |     |     | 510 |     |     |
| Gly | His | Pro | Ala | Arg | Thr | Ala | Glu | Lys | Ser | Lys | His | Arg | Arg | Leu | Asp |
|     |     | 515 |     |     |     |     | 520 |     |     |     |     | 525 |     |     |     |
| Arg | Leu | Gly | Gly | Thr | Leu | Arg | Trp | Lys | Arg | Gln | Pro | Ala | Thr | Pro | Ala |
|     |     | 530 |     |     |     | 535 |     |     |     |     | 540 |     |     |     |     |
| Leu | Met | Ser | Lys | Cys | His | Phe | Ser | Leu | Ala | Ala | Ala | Met | Arg | His | Lys |
| 545 |     |     |     |     | 550 |     |     |     |     | 555 |     |     |     |     | 560 |
| Ser | Lys | Pro | Met | Ser | Lys | Ala | Leu | Pro | Cys | Trp | Asn | Arg | Ser | Gln | Met |
|     |     |     |     | 565 |     |     |     |     | 570 |     |     |     |     | 575 |     |
| Ala | Ser | Ala | Thr | Ile | Lys | Ser | Lys | Ser | Thr | Arg | Phe | Arg | Arg | Lys | Ser |
|     |     |     | 580 |     |     |     |     | 585 |     |     |     |     | 590 |     |     |
| Cys | Ser | Ser | Thr | Lys | Pro | Ser | Ser | Ala | Asp | Arg | Pro | Arg | Asn | Asp |
|     |     |     | 595 |     |     |     |     | 600 |     |     |     |     | 605 |     |     |
| Gly | Leu | Ser | Trp | Arg | Phe | Ala | Arg | Val | Gly | Pro | Asn | Tyr | Arg | His | Leu |
|     |     | 610 |     |     |     |     | 615 |     |     |     |     | 620 |     |     |     |
| Pro | His | Gly | Val | Phe | Thr | Asp | Arg | Ile | Gly | Val | Leu | Thr | Asn | Asp | Phe |
| 625 |     |     |     |     | 630 |     |     |     |     | 635 |     |     |     |     | 640 |
| Phe | Val | Asn | Leu | Leu | Asp | Met | Asn | Tyr | Glu | Trp | Val | Pro | Thr | Asp | Ser |
|     |     |     |     | 645 |     |     |     |     | 650 |     |     |     |     | 655 |     |
| Gly | Ile | Tyr | Glu | Ile | Arg | Asp | Arg | Lys | Thr | Gly | Glu | Val | Arg | Trp | Thr |
|     |     |     | 660 |     |     |     |     | 665 |     |     |     |     | 670 |     |     |
| Ala | Thr | Arg | Val | Asp | Leu | Ile | Phe | Gly | Ser | Asn | Ser | Ile | Leu | Arg | Ser |
|     |     | 675 |     |     |     |     | 680 |     |     |     |     | 685 |     |     |     |
| Tyr | Ala | Glu | Phe | Tyr | Ala | Gln | Asp | Asn | Gln | Glu | Lys | Phe | Val | Arg |
|     |     | 690 |     |     |     |     | 695 |     |     |     |     | 700 |     |     |     |
| Asp | Phe | Ile | Asn | Ala | Trp | Val | Lys | Val | Met | Asn | Ala | Asp | Arg | Phe | Asp |
| 705 |     |     |     |     | 710 |     |     |     |     | 715 |     |     |     |     | 720 |
| Leu | Val | Lys | Lys | Ala | Arg | Glu | Ser | Val | Thr | Ala |
|     |     |     |     | 725 |     |     |     |     | 730 |     |

( 2 ) INFORMATION FOR SEQ ID NO:16:

( i ) SEQUENCE CHARACTERISTICS:
        ( A ) LENGTH: 294 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

| Thr | Thr | Pro | Leu | Val | His | Val | Ala | Ser | Val | Glu | Lys | Gly | Arg | Ser | Tyr |
| 1 |     |     |     | 5 |     |     |     |     | 10 |     |     |     |     | 15 |     |
| Glu | Asp | Phe | Gln | Lys | Val | Tyr | Asn | Ala | Ile | Ala | Leu | Lys | Leu | Arg | Glu |
|     |     |     | 20 |     |     |     |     | 25 |     |     |     |     | 30 |     |     |
| Asp | Asp | Glu | Tyr | Asp | Asn | Tyr | Ile | Gly | Tyr | Gly | Pro | Val | Leu | Val | Arg |
|     |     | 35 |     |     |     |     | 40 |     |     |     |     | 45 |     |     |     |
| Leu | Ala | Trp | His | Ile | Ser | Gly | Thr | Trp | Asp | Lys | His | Asp | Asn | Thr | Gly |
|     | 50 |     |     |     |     | 55 |     |     |     |     | 60 |     |     |     |     |
| Gly | Ser | Tyr | Gly | Gly | Thr | Tyr | Arg | Phe | Lys | Lys | Glu | Phe | Asn | Asp | Pro |
| 65 |     |     |     |     | 70 |     |     |     |     | 75 |     |     |     |     | 80 |

| | | | | | | | | | | | | | | |
|---|---|---|---|---|---|---|---|---|---|---|---|---|---|---|
|Ser|Asn|Ala|Gly|Leu 85|Gln|Asn|Gly|Phe|Lys 90|Phe|Leu|Glu|Pro|Ile His 95|
|Lys|Glu|Phe|Pro 100|Trp|Ile|Ser|Ser|Gly 105|Asp|Leu|Phe|Ser|Leu 110|Gly Gly|
|Val|Thr|Ala 115|Val|Gln|Glu|Met|Gly 120|Gly|Pro|Lys|Ile|Pro 125|Trp|Arg Cys|
|Gly|Arg 130|Val|Asp|Thr|Pro|Glu 135|Asp|Thr|Thr|Pro|Asp 140|Asn|Gly|Arg Leu|
|Pro 145|Asp|Ala|Asp|Lys|Asp 150|Ala|Gly|Tyr|Val|Arg 155|Thr|Phe|Phe|Gln Arg 160|
|Leu|Asn|Met|Asn|Asp 165|Arg|Glu|Val|Val|Ala 170|Leu|Met|Gly|Ala|His Ala 175|
|Leu|Gly|Lys|Thr 180|His|Leu|Lys|Asn|Ser 185|Gly|Tyr|Glu|Gly|Pro 190|Trp Gly|
|Ala|Ala|Asn 195|Asn|Val|Phe|Thr|Asn 200|Glu|Phe|Tyr|Leu|Asn 205|Leu|Leu Asn|
|Glu|Asp 210|Trp|Lys|Leu|Glu|Lys 215|Asn|Asp|Ala|Asn|Asn 220|Glu|Gln|Trp Asp|
|Ser 225|Lys|Ser|Gly|Tyr|Met 230|Met|Leu|Pro|Thr|Asp 235|Tyr|Ser|Leu|Ile Gln 240|
|Asp|Pro|Lys|Tyr|Leu 245|Ser|Ile|Val|Lys|Glu 250|Tyr|Ala|Asn|Asp|Gln Asp 255|
|Lys|Phe|Phe|Lys 260|Asp|Phe|Ser|Lys|Ala 265|Phe|Glu|Lys|Leu|Leu 270|Glu Asn|
|Gly|Ile|Thr 275|Phe|Pro|Lys|Asp|Ala 280|Pro|Ser|Pro|Phe|Ile 285|Phe|Lys Thr|
|Leu|Glu 290|Glu|Gln|Gly|Leu| | | | | | | | | |

( 2 ) INFORMATION FOR SEQ ID NO:17:

( i ) SEQUENCE CHARACTERISTICS:
        ( A ) LENGTH: 652 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

| | | | | | | | | | | | | | | |
|---|---|---|---|---|---|---|---|---|---|---|---|---|---|---|
|Met 1|Ser|Thr|Asp|Asp 5|Thr|His|Asn|Thr|Thr 10|Lys|Cys|Pro|Phe|His Gln 15|
|Gly|Gly|His|Asp 20|Gln|Ser|Ala|Gly|Ala 25|Gly|Thr|Thr|Asn|Arg 30|Asp Trp|
|Trp|Pro|Asn 35|Gln|Leu|Asp|Leu|Leu 40|His|Gln|His|Ser|Asn 45|Arg|Ser Asn|
|Pro|Leu 50|Gly|Glu|Asp|Phe|Asp 55|Tyr|Lys|Glu|Phe|Ser 60|Lys|Leu|Asp Tyr|
|Tyr 65|Ala|Leu|Lys|Asp|Leu 70|Lys|Ala|Leu|Leu|Thr 75|Glu|Ser|Gln|Pro Trp 80|
|Trp|Pro|Ala|Asp|Tyr 85|Gly|Tyr|Gly|Pro|Leu 90|Phe|Ile|Arg|Met|Ala Trp 95|
|His|Gly|Ala|Gly 100|Thr|Tyr|Arg|Asp|Gly 105|Arg|Gly|Gly|Ala|Gly 110|Gly Gln|
|Arg|Phe|Ala 115|Pro|Leu|Asn|Ser|Trp 120|Pro|Asp|Asn|Ala|Ser 125|Leu|Asp Lys|
|Ala|Arg 130|Arg|Leu|Leu|Trp|Pro 135|Ile|Lys|Lys|Tyr|Gly 140|Gln|Lys|Ile Ser|

| Trp | Ala | Asp | Leu | Phe | Ile | Leu | Ala | Gly | Asn | Val | Ala | Leu | Glu | Asn | Phe |
| 145 | | | | | 150 | | | | | 155 | | | | | 160 |
| Arg | Gly | Phe | Ala | Gly | Arg | Thr | Glu | Asp | Val | Trp | Glu | Pro | Asp | Leu | Asp |
| | | | | 165 | | | | | 170 | | | | | 175 | |
| Val | Asn | Trp | Gly | Glu | Lys | Ala | Trp | Leu | Thr | His | Arg | His | Pro | Glu | Leu |
| | | | 180 | | | | | 185 | | | | | 190 | | |
| Ala | Lys | Ala | Pro | Leu | Gly | Ala | Thr | Glu | Met | Gly | Leu | Ile | Tyr | Val | Asn |
| | | 195 | | | | | 200 | | | | | 205 | | | |
| Pro | Glu | Gly | Pro | Asn | His | Ser | Pro | Leu | Ser | Ala | Ala | Ala | Ala | Ile | Arg |
| | 210 | | | | | 215 | | | | | 220 | | | | |
| Thr | Phe | Arg | Met | Gly | Met | Asn | Asp | Glu | Glu | Thr | Val | Ala | Leu | Ile | Ala |
| 225 | | | | | 230 | | | | | 235 | | | | | 240 |
| Gly | Gly | His | Thr | Leu | Gly | Lys | Thr | His | Gly | Ala | Gly | Pro | Ala | Ser | His |
| | | | | 245 | | | | | 250 | | | | | 255 | |
| Val | Gly | Pro | Pro | Glu | Ala | Ala | Pro | Ile | Glu | Ala | Gln | Gly | Leu | Gly | Trp |
| | | | 260 | | | | | 265 | | | | | 270 | | |
| Ala | Ser | Ser | Tyr | Gly | Ser | Gly | Val | Gly | Ala | Asp | Ala | Ile | Thr | Ser | Gly |
| | | 275 | | | | | 280 | | | | | 285 | | | |
| Glu | Val | Val | Trp | Thr | Gln | Thr | Pro | Thr | Gln | Trp | Asn | Phe | Phe | Glu | Asn |
| | 290 | | | | | 295 | | | | | 300 | | | | |
| Leu | Phe | Tyr | Glu | Trp | Val | Leu | Thr | Lys | Ser | Pro | Ala | Gly | Ala | Gln | Glu |
| 305 | | | | | 310 | | | | | 315 | | | | | 320 |
| Ala | Val | Asp | Gly | Ala | Pro | Asp | Ile | Ile | Pro | Asp | Pro | Phe | Asp | Pro | Ser |
| | | | | 325 | | | | | 330 | | | | | 335 | |
| Lys | Lys | Arg | Lys | Pro | Thr | Met | Leu | Val | Thr | Asp | Leu | Leu | Arg | Phe | Asp |
| | | | 340 | | | | | 345 | | | | | 350 | | |
| Pro | Glu | Tyr | Glu | Lys | Ile | Ser | Arg | Arg | Phe | Leu | Asn | Asp | Pro | Glu | Phe |
| | | 355 | | | | | 360 | | | | | 365 | | | |
| Glu | Ala | Phe | Ala | Arg | Ala | Trp | Phe | Lys | Leu | Thr | His | Arg | Asp | Met | Gly |
| | 370 | | | | | 375 | | | | | 380 | | | | |
| Pro | Lys | Arg | Tyr | Ile | Gly | Pro | Glu | Val | Pro | Lys | Glu | Asp | Leu | Ile | Trp |
| 385 | | | | | 390 | | | | | 395 | | | | | 400 |
| Gln | Asp | Pro | Pro | Gln | Tyr | Pro | Thr | Glu | Asp | Ile | Ile | Leu | Lys | Ala | Ala |
| | | | | 405 | | | | | 410 | | | | | 415 | |
| Ile | Ala | Ala | Ser | Gly | Leu | Val | Ser | Glu | Leu | Val | Ser | Ala | Trp | Ala | Ser |
| | | | 420 | | | | | 425 | | | | | 430 | | |
| Ala | Ser | Thr | Phe | Arg | Gly | Gly | Asp | Lys | Arg | Gly | Gly | Ala | Asn | Gly | Ala |
| | | 435 | | | | | 440 | | | | | 445 | | | |
| Arg | Leu | Ala | Pro | Gln | Arg | Asp | Trp | Val | Asn | Pro | Ala | Ala | Arg | Val | Leu |
| | 450 | | | | | 455 | | | | | 460 | | | | |
| Val | Leu | Glu | Glu | Ile | Gln | Thr | Lys | Ala | Ser | Leu | Ala | Asp | Ile | Val | Leu |
| 465 | | | | | 470 | | | | | 475 | | | | | 480 |
| Gly | Val | Val | Gly | Glu | Lys | Ala | Ala | Ala | Ala | Gly | Leu | Ser | Ile | His |
| | | | | 485 | | | | | 490 | | | | | 495 | |
| Val | Pro | Phe | Ala | Pro | Gly | Arg | Asp | Ala | Arg | Gln | Asp | Gln | Thr | Asp | Ile |
| | | | 500 | | | | | 505 | | | | | 510 | | |
| Glu | Met | Phe | Leu | Leu | Glu | Pro | Ile | Ala | Asp | Gly | Phe | Arg | Asn | Tyr | Arg |
| | | 515 | | | | | 520 | | | | | 525 | | | |
| Ala | Leu | Asp | Val | Ser | Thr | Thr | Glu | Ser | Leu | Ile | Asp | Lys | Ala | Gln | Gln |
| | 530 | | | | | 535 | | | | | 540 | | | | |
| Leu | Thr | Leu | Ala | Pro | Glu | Met | Thr | Val | Leu | Val | Gly | Gly | Met | Arg | Val |
| 545 | | | | | 550 | | | | | 555 | | | | | 560 |
| Leu | Gly | Asn | Asp | Gly | Pro | Asn | Gly | Val | Phe | Thr | Asp | Arg | Gly | Val | Leu |

-continued

|   |   |   |   |   | 565 |   |   |   |   |   | 570 |   |   |   |   |   | 575 |   |
|---|---|---|---|---|---|---|---|---|---|---|---|---|---|---|---|---|---|---|
| Asn | Asp | Phe | Phe<br>580 | Val | Asn | Leu | Leu | Asp<br>585 | Met | Arg | Tyr | Glu | Trp<br>590 | Lys | Pro |
| Thr | Asp | Leu<br>595 | Glu | Gly | Arg | Asp | Arg<br>600 | Thr | Gly | Glu | Val | Lys<br>605 | Trp | Thr | Ala |
| Arg | Asp<br>610 | Leu | Val | Phe | Gly | Ser<br>615 | Asn | Ser | Val | Leu | Arg<br>620 | Ala | Leu | Ala | Glu |
| Val<br>625 | Tyr | Ala | Ser | Asp | Ala<br>630 | Glu | Lys | Phe | Val | Lys<br>635 | Asp | Phe | Val | Ala | Ala<br>640 |
| Trp | Val | Lys | Val | Met<br>645 | Asn | Leu | Asp | Arg | Phe<br>650 | Asp | Leu |

What is claimed is:

1. A nucleic acid probe for detecting *Mycobacterium tuberculosis* resistant to isoniazid, wherein said probe is selected from the group consisting of a 3.1 kb KpnI-BamHI fragment of plasmid pYZ57, a 2.5 EcoRV-KpnI fragment of plasmid pYZ55, and a 2.5 kb EcoRV-KpnI fragment of plasmid pYZ56.

2. The probe as claimed in claim 1, which is DNA free of human serum proteins, viral proteins, bacterial proteins, and nucleotide sequences encoding said proteins.

3. The probe as claimed in claim 1, which is free of human tissue.

4. The probe as claimed in claim 1 having radionuclide label bonded to the probe.

5. A nucleotide sequence, which is a 350 base sequence as described in FIG. 6(c) (SEQ ID NO:3).

6. A method for the detection of the presence of nucleic acids of *Mycobacterium tuberculosis* in a sample, which is resistant to isoniazid, comprising contacting the sample with the probe of claim 1 or the nucleotide sequence of claim 5 under hybridization conditions, and detecting a hybrid formed between the nucleic acid of *Mycobacterium tuberculosis* resistant to isoniazid in the sample and the probe.

7. The method of claim 6, wherein said probe is labeled.

8. The method of claim 7, wherein said label is either capable of being detected or is capable of selectively bonded to an indicator to form a detectable complex.

9. The method of claim 8, wherein said probe is labeled with a radioactive isotope.

10. The method of claim 9, wherein said label is a non-isotopic marker and said indicator is avidin to which is bonded a chemical entity which, when said avidin is bonded to said marker on said hybrid DNA complex, is capable of being detected.

11. The method of claim 10, wherein said chemical entity is a fluorophore, which renders said hybrid DNA complexes fluorometrically detectable.

12. The method of claim 10, wherein said chemical entity is an electron-dense compound, which renders said hybrid DNA complexes detectable by an electron microscope.

13. The method of claim 10, wherein said chemical entity is an antibody, which renders said hybrid DNA complexes immunologically detectable.

14. The method of claim 10, wherein said chemical entity is one of a catalyst/substrate pair, which renders hybrid DNA complexes enzymatically detectable.

* * * * *

UNITED STATES PATENT AND TRADEMARK OFFICE
CERTIFICATE OF CORRECTION

PATENT NO. : 5,871,912
DATED : February 16, 1999
INVENTOR(S) : HEYM et al.

It is certified that error appears in the above-identified patent and that said Letters Patent is hereby corrected as shown below:

Title Page: under the heading "Assignee:", after "Institut Pasteur, Paris Cedex, France", please insert:

-- Assistance Publique, France,
Universite Paris VI, France, and
Medical Research Council, Great Britain --.

Signed and Sealed this

Eighteenth Day of July, 2000

Attest:

Q. TODD DICKINSON

*Attesting Officer*    *Director of Patents and Trademarks*